(12) United States Patent
Wig et al.

(10) Patent No.: US 8,053,630 B2
(45) Date of Patent: Nov. 8, 2011

(54) NEMATODE INDUCIBLE PLANT METABOLITE EXPORTER GENE PROMOTERS

(75) Inventors: Aaron Wig, Chapel Hill, NC (US); Robert Ascenzi, Cary, NC (US); Sumita Chaudhuri, Cary, NC (US); Xiang Huang, Apex, NC (US); Rui-Guang Zhen, Chapel Hill, NC (US); Yu Han, Research Triangle Park, NC (US)

(73) Assignee: BASF Plant Science GmbH (DE)

( * ) Notice: Subject to any disclaimer, the term of this patent is extended or adjusted under 35 U.S.C. 154(b) by 329 days.

(21) Appl. No.: 12/280,186

(22) PCT Filed: Feb. 13, 2007

(86) PCT No.: PCT/EP2007/051378
§ 371 (c)(1),
(2), (4) Date: Oct. 10, 2008

(87) PCT Pub. No.: WO2007/096275
PCT Pub. Date: Aug. 30, 2007

(65) Prior Publication Data
US 2009/0089896 A1    Apr. 2, 2009

Related U.S. Application Data

(60) Provisional application No. 60/743,341, filed on Feb. 23, 2006.

(51) Int. Cl.
*A01H 5/00*  (2006.01)
*A01H 1/00*  (2006.01)
*C07H 21/04* (2006.01)

(52) U.S. Cl. ....... 800/278; 800/287; 800/298; 536/24.1; 435/320.1; 435/410

(58) Field of Classification Search .................. None
See application file for complete search history.

(56) References Cited

U.S. PATENT DOCUMENTS

| | | |
|---|---|---|
| 5,023,179 A | 6/1991 | Lam et al. |
| 5,457,178 A | 10/1995 | Jackson et al. |
| 5,589,622 A | 12/1996 | Gurr et al. |
| 5,695,954 A | 12/1997 | Sherwood et al. |
| 5,750,386 A | 5/1998 | Conkling et al. |
| 5,763,568 A | 6/1998 | Atkinson et al. |
| 5,824,876 A | 10/1998 | Gurr et al. |
| 5,837,876 A | 11/1998 | Conkling et al. |
| 5,866,777 A | 2/1999 | Sijmons et al. |
| 5,955,646 A | 9/1999 | Gelvin et al. |
| 5,959,182 A | 9/1999 | Atkinson et al. |
| 6,005,092 A | 12/1999 | Shoseyov et al. |
| 6,262,344 B1 | 7/2001 | Ohl et al. |
| 6,395,963 B1 | 5/2002 | Ohl et al. |
| 6,448,471 B1 | 9/2002 | Puzio et al. |
| 6,593,513 B2 | 7/2003 | Davis et al. |
| 6,906,241 B2 | 6/2005 | Davis et al. |
| 7,078,589 B2 | 7/2006 | Hu et al. |
| 2003/0167507 A1 | 9/2003 | Odell et al. |
| 2004/0029167 A1 | 2/2004 | Fritig et al. |
| 2004/0078841 A1 | 4/2004 | Atkinson et al. |
| 2004/0248304 A1 | 12/2004 | Hu et al. |
| 2005/0070697 A1 | 3/2005 | Hu et al. |
| 2005/0188438 A1 | 8/2005 | Ren et al. |
| 2005/0262585 A1 | 11/2005 | MacKenzie et al. |

FOREIGN PATENT DOCUMENTS

| | | |
|---|---|---|
| WO | WO-94/10320 A1 | 5/1994 |
| WO | WO-98/31822 A1 | 7/1998 |
| WO | WO-99/28483 A2 | 6/1999 |
| WO | WO-02/16655 A2 | 2/2002 |
| WO | WO-03/033651 A2 | 4/2003 |
| WO | WO-2004/029222 A2 | 4/2004 |

OTHER PUBLICATIONS

Database GenEmbl, Accession No. AC013483, Jun. 28, 2000.*
Bustos et al, The EMBO Journal (1991) vol. 10, pp. 1469-1479.*
Donald et al, 1990, EMBO J. 9:1717-1726.*
Chen et al, 2000, Sex. Plant Reprod. 13:85-94.*
Benfey et al, 1990, Science 250:959-966, see Abstract, Fig. 3-5.*
Kim et al, 1994, Plant Mol. Biol. 24:105-117.*
U.S. Appl. No. 60/743,341, filed Feb. 23, 2006, BASF Plant Science GmbH.
U.S. Appl. No. 60/743,340, filed Feb. 23, 2006, BASF Plant Science GmbH.
Huang, H., et al., "DNA Binding Properties of Two Arabidopsis MADS Domain Proteins: Binding Consensus and Dimer Formation", The Plant Cell, vol. 8, (1996), pp. 81-94.
Toyofuku, K, et al., "Promoter Elements Required for Sugar-Repression of the *RAmy3D* Gene for alpha-amylase in Rice", FEBS Letters, vol. 428, (1998), pp. 275-280.
Morita, A., et al., "Functional Dissection of a Sugar-Repressed alpha-amylase Gene (*RAmy1A*) Promoter in Rice Embryos", FEBS Letters, vol. 423, (1998), pp. 81-85.
Gubler, F., et al., "Gibberellin-Responsive Elements in the Promoter of a Barley High-pl alpha-Amylase Gene", The Plant Cell, vol. 4, (1992), pp. 1435-1441.
Lanahan, M. B., et al., "A Gittherellin Response Complex in Cereal alpha-Amylase Gene Promoters", The Plant Cell, vol. 4, (1992), pp. 203-211.
Huttly, A.K., "Sequence Heterogeneity and Differential Expression of the *alpha-Amy2* Gene Family in Wheat", Mol. Gen. Genet., vol. 214, (1988), pp. 232-240.
Isabel-Lamoneda, I., et al., "SAD: A New DOF Protein from Barley that Activates Transcription of a Cathepsin B-like Thiol Protease Gene in the Aleurone of Germinating Seeds", The Plant Journal, vol. 33, (2003), pp. 329-340.

(Continued)

*Primary Examiner* — Eileen B O Hara
(74) *Attorney, Agent, or Firm* — Connolly Bove Lodge & Hutz LLP

(57) ABSTRACT

The invention provides plant gene promoters, and essential promoter elements, which are root-specific and/or induced by parasitic nematodes. The promoters of the invention are useful for controlling expression of nucleic acids of interest in plant roots.

17 Claims, 22 Drawing Sheets

OTHER PUBLICATIONS

Lu, C.-A., et al., "Three Novel MYB Proteins with One DNA Binding Repeat Mediate Sugar and Hormone Regulation of alpha-Amylase Gene Expression", The Plant Cell, vol. 14, (2002), pp. 1963-1980.

Yanagisawa, S., et al., "Diversity and Similarity Among Recognition Sequences of Dof Transcription Factors", The Plant Journal, vol. 17, No. 2, (1999), pp. 209-214.

Neto, G.C., et al., "The involvement of Opaque 2 in β-prolamin Gene Regulation in Maize and Coix Suggests a more General Role for this Transcriptional Activator", Plant Molecular Biology, vol. 27, (1995), pp. 1015-1029.

Vincentz, M., et al., "ACGT and Vicilin Core Sequences in a Promoter Domain Required for Seed-Specific Expression of a 2S Storage Protein Gene are Recognized by the Opaque-2 Regulatory Protein", Plant Molecular Biology, vol. 34, (1997), pp. 879-889.

Hwang, Y.-S., "The Maize O2 and PBF Proteins Act Additively to Promote Transcription from Storage Protein Gene Promoters in Rice Endosperm Cells", Plant Cell Physiol., vol. 45, No. 10, (2004), pp. 1509-1518.

Hong., R.L., et al., "Regulatory Elements of the Floral Homeotic Gene AGAMOUS Identified by Phylogenetic Footprinting and Shadowing", The Plant Cell., vol. 15, (2003), pp. 1296-1309.

Lohmann, J.U., et al., "A Molecular Link between Stem Cell Regulation and Floral Patterning in *Arabidopsis*", Cell, vol. 105, (2001), pp. 793-803.

Riechmann, J.L., et al., "DNA-binding Properties of *Arabidopsis* MADS Domain Homeotic Proteins APETALA1, APETALA3, PISTILLATA and AGAMOUS", Nucleic Acids Research, vol. 24, No. 16, (1996), pp. 3134-3141.

Hill, T.A., et al., "Discrete Spatial and Temporal *cis*-acting Elements Regulate Transcription of the *Arabidopsis* Floral Homeotic Gene *APETALA3*", Development, vol. 125, (1998), pp. 1711-1721.

Sessa, G., et al., "The Athb-1 and -2 HD Zip Domains Homodimerize Forming Complexes of Different DNA Binding Specificities", The EMBO Journal, vol. 12, No. 9, (1993), pp. 3507-3517.

Gidoni, D., et al., "Novel *cis*-acting Elements in Petunia *Cab* Gene Promoters", Mol. Gen. Genet, vol. 215, (1989), pp. 337-344.

Yang, H., et al., "Molecular Cloning and Characterization of *OsPSK*, a Gene Encoding a Precursor for Phytosulfokine-alpha, Required for Rice Cell Proliferation", Plant Molecular Biology, vol. 635, (2000), pp. 635-647.

Chiron, H., et al., "Gene Induction of Stilbene Biosynthesis in Scots Pine in Response to Ozone Treatment, Wounding, and Fungal Infection", Plant Physiology, vol. 124, (2000), pp. 865-872.

Guerineau, F., et al., "A Jasmonate-Responsive Element with the *A. thaliana vsp1* Promoter", Journal of Experimental Botany, vol. 54, No. 385, (2003), pp. 1153-1162.

Haralampidis, K., et al., "Combinatorial Interaction of Cis Elements Specifies the Expression of the *Arabidopsis AtHsp90-1* Gene", Plant Physiology, vol. 129, (2002), pp. 1138-1149.

Ishizaka, T., et at Characterisation of the *S*-RNase Promoters from Sweet Cherry (*Prunus avium L.*), Genes Genet. Syst., vol. 78, (2003), pp. 191-194.

Hasegawa, K., et al., "In Vitro Analysis of Transcription Initiation and Termination from the *Lhcb1* Gene Family in *Nicotiana sylvestris*: Detection of Transcription Termination Sites", The Plant Journal, vol. 33, (2003), pp. 1063-1072.

Sessa, G., et al., "The *Arabidopsis Athb-8*, *-9* and *-14* Genes are Members of a Small Gene Family Coding for Highly Related HD-ZIP Proteins", Plant Molecular Biology, vol. 38, (1998), pp. 609-622.

"Sequence 4341 from Patent WO0216655", EMBL Database, Accession No. AX509646, Sep. 27, 2002.

"Genomic sequence for *Arabidopsis thaliana* BAC T26F17 from chromosome I, complete sequence", EMBL Database, Accession No. AC013482, Nov. 15, 1999.

Terada, R., et al., "Expression of Early Nodulin Promoter Gene in Transgenic Rice", Current Science, vol. 81, No. 3, (2001), pp. 270-276.

Favery, B., at al., "Characterisation of Plant Genes Involved in Giant Cells Formation Induced by Root-knot Nematodes in *Arabidopsis thaliana* and *Medicago truncatula*", Nematology Monographs & Perspectives, vol. 2, (2004), pp. 351-358.

* cited by examiner

Figure 1A

| | |
|---|---|
| 1 | CAGACAAAGA ATTATTGGAA AACAATGAGA ATTTTTGACG GTGGTTTGTT ATAATGTATT |
| 61 | ATTAAATAAC ATGATAATGG AAATTACTTT GTTTTAGTTA AAGGAAAATT AATTTGTTGT |
| 121 | TTAATAAACT AGTGGTAGGT AGGAATAGTT AAAATGTAAG TATCAAAGTT TTTTGAATTT |
| 181 | AAGATTAAGA TTCTCGAAAT TCAGTTATTA GCATACAAAT GACATAAATT ATGAAAAAAT |
| 241 | AAATTAAAAT AATGTCATAC AGATCCAGAT GAAAATGTAT AATGTATATA CATTTGATAA |
| 301 | AAATGAAAAT GTATTTTCGG GTTCTCAGTT TGTTTTGTGA AATATCAATA CACAATGTTA |
| 361 | AAAAAGAATC GGCTTCTTTC AGCTTATGAT ATTCATTAAT TTTCCACACA CCATTTTTCA |
| 421 | AAGGGAAATA GCAAAAAAAA TTAAAATTAA AACAGCCAGC TAAATTAATC AGTGAAATCA |
| 481 | TCCAAACTGT TTTACAAAGA CATTTTTTCG GCCAAATCAA ATAAAAAAAT CGATTGTTAT |
| 541 | TGACAGTCTT TGTGATCTTA TTGGTTACGT TATACCCACC TGTGCACTCC ACTTTTAAGT |
| 601 | ACTACTTCGT CTCTAAATAT GGTACGGACT AACTTGAAAT TAGCCTATTG ATTTGCTTAG |
| 661 | AAATTGATAA ATCTTTGGAC GAGATGGTGT CCACTCTTTA AATCACCACA ATGTCCCCTA |
| 721 | TCTATTTTCC GCGACAAGAT GAATAAGAAT ATGCACTAAA CTTAACCATC ATTCGCTTAT |
| 781 | ACACTATATT TATTAAATCA GCTTTCTCAT CGCCTAAAAT TCAATATTTT TGGGTCCATT |
| 841 | ATCTACACGA CACAATGGAT CATTCACATA CGGCCGCGCA TCAAATGATT TCGTAAGTCC |
| 901 | CGGCAAATGT TAATAAACTA TTTGAAAAAG AAAGAGTCAT GTGTCCCGTC AATTCAAGTA |
| 961 | CTTATTTATT GTGATTTTTT GCACATATAT AGATTAACAT ATATTCATGG TTAAAACTTG |
| 1021 | TTGATGCTGC AAAAAGGATA ATTATCACCC ACGTACATTA CTCATATGAA TATAAAAGGT |
| 1081 | GCATAATTTT TTTTTTTTTT TTTGTAATGT TTTATGTATA TACACATATA GTATACCAAT |
| 1141 | TTTTTAACAA AACAAATTAC ATATAGATAA CAAAGAGGTG AATAGTTTCG ATCGTGAATA |
| 1201 | TTCAGGTTGA TACTAATTAG TTCTCCTTTT GTAGATTCGA CAAGTGTGAT GAGTGGATAA |
| 1261 | AAAAATGGAT GACGTCTTGA GTGGATTGTA CATATACAAA TAGATAATGT AAGTGCATGC |
| 1321 | TTTTTGATTC TTCGAAACTA TTTGGTTATA ACTTTCGGAT ATACTTATAA CAAAAAAAAA |
| 1381 | AACCTTTCGG ATATACATGG TTCGGCTTGG ACGTACAGGT CTATATAATA ATTTGATATA |
| 1441 | TATTGGTACA TTTCATTTAT ATACTCTTTA TTGGTACGAT ACATTTGAT TCGTTATCAA |
| 1501 | TATATtaata ccacattgac gaGAACATTC TCATTAGTGA TCgtagatta ataatCTAGC |
| 1561 | CATCTTAATA AGCAAAATAT Ataatccaaa aaatgcgaca ttattttacA TACGCAAGTG |
| 1621 | TTCACAACCA ATAGTCCaat atataaatta atTAAGTAGG TATGTAATAT AACCAAGGAA |
| 1681 | ATTACGATCT AATCCAGTTT TGATTACCTA GAACAAGACC ATAGTTAGCC ACACATAATG |
| 1741 | GATACGTGCT TGACAACAAT TAAAACCTA TATTTTAAA AGTGATGCTT AAATAGCCAA |
| 1801 | TGGATTGAAA TGTGCACTCG CATATATTGC TTTTTGTGTC AGCACAATTT GGCtatataa |
| 1861 | GCAAGTACTC TCTTGTAGTA ATCATTCACA GTCATAACTA ATTAAGTACA TTTGAATACA |
| 1921 | TCAAATACCA AGAAAGAGAA ATTTAGAGAG AAAGAGAAAG AGATAAA (SEQ ID NO:1) |

Figure 1B

| Element class | Location | Highlight | Promoter Configuration |
|---|---|---|---|
| P$MADS | 1714-1734 | bold | 1 and 3 |
| P$MYBS | 1733-1749(minus strand) | bold and underline | 1 |
| P$DOFF | 1771-1787 | bold and italic | 1 and 3 |
| P$OPAQ | 1506-1522 | Lower case | 2 |
| P$AHPB | 1543-1555(minus strand) | Lower case and bold | 2 |
| P$MADS | 1582-1602 | Lower case and italic | 2 |
| P$AHPB | 1597-1609 | Lower case and underline | 2 |
| P$TBPF | 1638-1652 | Lower case, bold, and underline | 2 and 3 |
| P$AHPB | 1697-1709 | underline | 3 |
| P$DOFF | 1825-1841(minus strand) | italic | 3 |
| P$AHPB | 1878-1890 | Underline and italic | 3 |

Figure 2

```
   1  CACTAATATA AGACATGGCA CGTTTGCATT ATGCTTCCTA TATTACCGAC TAAATTAGTG
  61  ATTGTCACAA GTAGCCGACA ACTTTTGGAC TTAATTAGCA ACAGACTTAT TGCTTCAGTA
 121  AGAAACCAAC AGATAAGCGA TGGGCATAAA TGGTATGTGG CTTTTTCATC CTGTTTTCAT
 181  GTTTTGAACG TCAAGAAAAA AAATTAATAA GGGATTTTTG AATCCATCCC GTACGTTTTA
 241  TATTTATAAA TAGTTTAGAT AAACCTTAAT TCCTCAACTA AATACTAGTT TCTTGGCATC
 301  TTATAAAGAA ACTATATGCA TTTTTATCCC TAATAATATA GTCTGTAGCG TATTTGCCTC
 361  CATATATTAT CGCCATATTA TCATAGACTG CATCTCATTT AGGGCGAATG TAATCATAGT
 421  TTTTGTAAAG AATTGAACTA CCTCTTCGCC TTTTTTTTTA TATAAGACAA TTCTTTAGTT
 481  TCTATCTATG GTTTAATTTG TATTTTGACG TGTATGGTAC TAATTAAGAT TATGCTATGT
 541  TTTGAGTTTT AGTTGAATAA AATTTAATTT GTAATAATTC TAAAACAATA AAAAGTTTAG
 601  TGTAATTTTT TTTAACTAGA ACGGATTAAG AGTTAGGACT GATGTTAGAA TCGCAGTTTT
 661  TTTTTTATGG AATGACGTAA AAGAATTCTT TAATAATCTT ACTTGGCAAT ATTAAATGGA
 721  ACAACTTAAA AGGACTAGAC AATATTATTG GCGTGATATC CAAATAATTA CGGTTAACA
 781  AAGAATAAAA TGGGGAAACC CTTTGGTATA TTGGTTATCT AAGAGTTCAT TAATATTTAT
 841  ATACATTAAG AGGTTAGAGT TTCGAGGTCA AGATATTATG TTTATTTAAA AATTTGCAGA
 901  TTAATAGAGA CAAGTGTGTA GGAGATCTCC AACGATATTC AATTATAACC GTTCGTCAGA
 961  ATTCTACGCA GATAGAACGT CGTTAGGTCA TAGATCATTG AAAGTGTCTA TCAAAAGCAT
1021  GGAGATTAAA AAAGAAAAAA GATTTGGAGA AGAAGTGAC TTTTGTCCTG GATCTATTAA
1081  GAGTCGAAAG AAATCGTCCG TTATACAATC GTGTATATAA CAATTCTCAT AATTTACAAT
1141  TTATAATACC GAAAAAATAT AAAACAAAAA AAAAATATTT TAAATAGAAC GAATCAGCCT
1201  CAACAAAAAC CTTTTTTGAA AATGGAAAAG CTTAGGCTGC TTTAACACGC CCAATCTCAC
1261  ACATACATAT TCTCTGTTTT CTTCTTTCCT TTTTGTAAAA GGGTTTGCTA ATTCTCTGCT
1321  TTGTTTTTTT TTTGTTTATT AATTCTTTAC ATTTCCTACA AAGAAAAAGA CAAGCATGAA
1381  TAACTAACAG CGGTTATACT GGAAATCCGA AGTCTTTTCC ACGTGCTTTC TGATGAACAT
1441  TTAACATAAA ACGTTCGGAC TCTTCGTGAC ACTTAAACCA AACATACACG TACGTAGCTA
1501  ACAATAGACG TGTAGATTTT AGGTTACGT GTTTTTCAAG TTGGGCAAGA ACAAAAAAAA
1561  AGAGAGCCTA TGACGTGTGC AACAGGATAA TAGTGTTAGC AAAAGAAATC ATCAGAGCCA
1621  TTATATGATA TTGTTTGCTT TTCAATTCCA TGAACGAACC CATACCAATC CAAAACAGCA
1681  ATTATCATCT TTCTTTATTG AACAAACGTA TCTCATTGGT CGTGTCCTAA TAAATAATTA
1741  TATTTCATAT ACATGTATAT ACTTTATAGT TTTTGTTTTT CCTTTTGCTA CTCTACATGA
1801  CTCTCGATCG AGGGAAAAAA CTAGTTCTCA TGTTTATCCA AAACTCTATA TCACCTTTTT
1861  GATGTTTTTA TATAAGAAGA CTTGTTCATC CATACTCTTT CAATAACCTT GACAGAAAAA
1921  AAAAATAAAC ACAAAATTTC AATAACC  (SEQ ID NO:2)
```

Figure 3

```
  1   GGTTACAGTA CCAATTCTGA AAAAACTTAA TGTTTAGATA AACTTTTTTA AAAAAAATAC
 61   TATTCGACTT GTTTAAAGTT AATGATATGA AATAAAATTT TCTATGAATT ACTTTTTGAG
121   TAAAACCATA TATGTGTACA GCAAAGTTTG AGAATAATTT ATCTCGATGG GAAGAAGAAA
181   AAAATGAAAG TATGAAATAA GATGGATGAT TGGATAAACT AAAAGAGATG AAAAAATATA
241   TATATAAATT ATTACAAAAA AAAAAAATCA TACAAGAATG ACATTACTGA AGCAAATTCG
301   CTTTCACATG AAAAGTATGC AGTGTAAAGA TATAAAAGTA AACCATTATT TTTGTCACTA
361   AAAAATGGAT ACAGAAAACC GAACATTAAA ACATGATCAT TCATTCACCA TTTTAAAATT
421   AAGATGATTA ATTTAAATAA AAAAATCATA TTAGATAAGT GATCAAAATA TTAGATAGTA
481   TAAAttaatt cacgtaacat aCACGCATTA ATCGCGCTTc ttgaatgatt agTCAGCAAT
541   TAAACCGTGC TAATTTCTTT TCTCACCTTC TAAtcttacc gctgccggga acgtGTAAAT
601   TAAGTAGCAT TGTAAAGCAG CTTTTTGGAT TATAaatatt attaaatATA CTCACGGGTt
661   gggtataaat attaAGATGG CCAGCATTGG TTTCGCAGGG AGTTGCAGAT AAACAAAATC
721   TAGCAGGAGC AAATTCACTT CTAAGATACA CATATTAAGT TCACCAGAGA GAGAGAGAGA
781   CATTAATCAA G (SEQ ID NO:3)
```

| Element class | Location | Highlight | Promoter Configuration |
|---|---|---|---|
| P$MADS | 173-193 | bold | 1 and 3 |
| P$MYBS | 205-221(minus strand) | bold and underline | 1 |
| P$DOFF | 214-230 | bold and italic | 1 and 3 |
| P$OPAQ | 485-501 | Lower case | 2 |
| P$AHPB | 520-532(minus strand) | Lower case and bold | 2 |
| P$MADS | 574-594 | Lower case and italic | 2 |
| P$AHPB | 635-647 | Lower case and underline | 2 and 3 |
| P$TBPF | 660-674 | Lower case, bold, and underline | 2 and 3 |
| P$AHPB | 522-534 | Underline and italic | 3 |
| P$DOFF | 616-632(minus strand) | italic | 3 |

Figure 4

```
   1  CACACAAGCA AATTCACTTC TCTGTTCTGA CACACATATT AAGTTCCCGA GAAAGATCTA
  61  GAGAGTAATT AAGATGGGTA CGTGGTTCAC AAATGCAAGG CCGTATCTGC TGTTAGTGGC
 121  AGTTCAATTT GGGTCTGCTG GCATGTTCAT ATTTGCGATG GATGCTATAA AGAAGGGTAT
 181  GAGCCATTAC GTGTTCATCG TCTATCGTAA TGCCATCGCC TCTGTATCTC TTGCTCCCTT
 241  CGCATTTGTT CTTGAAAGGA AGTTAGGCC CAAGATGACT TTCCGGGTAT TTTCAGAGAT
 301  TATGGCACTG GCTTTCTTCG AAATAATACT GGACCAGTGC TTCGCCCTCT TGGGCATGAA
 361  ATTCACGTCG GCATCTTTCC TATCTGCTGT TATGAACTCC GCTCCCTCTG TTACTTTTGT
 421  GATGGCTGTC ATTCTAAGAA TGGAGCACAT GAAGATTAAG GAGGTGGCAT GTCAAGCCAA
 481  AGTGATTGGC ACAGTAATAA CATTTGGAGG CACCTTGCTT ATGGCACTGT ACAAGGACC
 541  CGTTCTTAGT TTTATGCGAT CTTCAACTAG CCATCCTAGC CAACCTGAGA ATGTGGCCAC
 601  AGAAACTGGT AACCATTGGG TCATAGGGAC ATTGTTCCTC CTCATTGGTT GTGCTGGCTT
 661  TTCTGCATTT TACATATTAC AGGCCATAAC ATTGGAGAAA TACCCAGCAG AGATGTCTCT
 721  GGCCACTTGG GTTTGCTTTG TAGGAGCACT TCAAAGCTCT ATTGTTGCAA TCTTCGCAGA
 781  ACGCCACCAC CCTCATGCTT GGTCCCTTGG TTGGGATACA CGTCTCTTTG CTCCTGCTTA
 841  CGCGGGAATA GTTACGTCTG GAGTTCAGTA TTACATACAA GGCATGGTCT CAAAAATTAT
 901  GGGCCCAGTT ATTGTGACTG CTTTTAATCC CCTGCGTATG ATCATTGTTA CGGCCTTGGC
 961  CTGCATCATC TTATCTGAAC AACTCTTCCT TGGAAGTATT ATTGGAGCAA TAGTTGTGGT
1021  TCTTGGGCTT TATCTAGTTG TGTGGGGAAA AGCTAAAGAA CGTAGAGGTC TGATGACACC
1081  GTCCCCTGCA GAAAATAACT TTCCAGAAGA CCAACGACAG CTACCGGTCA CAGCTCCAAG
1141  GAATGATAGC ATTAACAATA ATAATAAGGC TTAATTAGTC CATCGCCATG ATGAAAAAG
1201  TGATGTGGAA GGCACAATAT ATCAAGAAGA GAAAGTCAGC AAAATTTAAG TAAAGGCCTC
1261  GGCTTTGTTT AATTAGACAT TGTTGTAGCA TTCCATACAA ATGATCTAAG GTCAATGTCA
1321  TGCACATTAC TAATACCATG AAATTGGTGG GATAAGTGGC ATGACGATTG ATGAAATTCA
1381 TCATATATAT AATTAATTAG TGGTCACTTT GAGCTGCAAA AAAAAAAAAA AAAAA
                                                          (SEQ ID NO:4)

1  TTCAAAGCTC TATTGTTGCA ATCTTCGCAG AACGCCACCA CCCTCATGCT TGGTCCCTTG
  61  GTTGGGATAC ACGACTCTTT GCTCCTGCTT ACGCGGGAAT AGTTACATCT GGAGTTCAGT
 121  ATTACATACA AGGCATGGTC TCAAAAATTA TGGGCCCAGT TATTGTGACT GCTTTTAATC
 181  CCCTGCGTAT GATCATTGTT ACGGCCTTGG CCTGCATCAT CTTATCCGAG CAACTCTTCC
 241  TTGGAAGTAT TATTGGAGCA GTAGTTGTGG TTCTTGGGCT TTATCTAGTT GTGTGGGGAA
 301  AAGCTAAAGA ACGCAGAGGT ATTATGACAC CGTCCCCTGC AGAAAATAAC TTTCCGGAAG
 361  ACCAACGACA GCTACCAGTC ATAGCTCCAA GGAATGATAA CATTAATACT AATAAGGCTT
 421  AATTAGTCCT TCGCCATGTT GAAAAACTG ATGTGGAAGG CACAATATAT CAAGAAGAGA
 481  GAGTCAGTAA AATTTAAGTA TAGGCCTAGG CTTTGTTTAA TTAGACATTG GTGTAGCATT
 541  CCGTACAAGT GATCTCAGGT CAATGTCATG CACATTACTA ATACCATGAA ATGGGTGGGA
 601  TAAGTGGCAT GACGATTGGT GAAATTCATC ATATATATAA TTAATTAGTG ATCAATTAGA
 661  GCTGCATCAT TGTTCTTGAG TTGAATGAAC TAATGTGCTT CCGAGTCATC ATAGAGTAAT
 721  TATTTACACA GTTCTGGGCT AATTTGCTTT CATATTCCAC TTTTAAGTAT TCCAATTCAG
 781  GGCTATAAAA AAAATGTATT CCATTTAAGC TAAGGTTGGA GATTTTAATA CAAGTCTAAA
 841 CATATATTTT TAGCAAAAAA AAAAAAAAAA A      (SEQ ID NO:5)
```

Figure 5

| | |
|---|---|
| 1 | ACTATAGGGC ACGCGTGGTC GACGGCCCGG GCTGGTATCA TAATTTTATT TATTTATTTA |
| 61 | TTTATTTTTG TGTCTCCATT CTATTGTAAA AATGAAATAA TGTAAAACGA GTTTTGTTAT |
| 121 | TTTATGGTTA CAGTACCAAT TCTGAAAAAA CTTAATGTTT AGATAAACTT TTTTAAAAAA |
| 181 | AATACTATTC GACTTGTTTA AAGTTAATGA TATGAAATAA AATTTTCTAT GAATTACTTT |
| 241 | TTGAGTAAAA CCATATATGT GTACAGCAAA GTTTGAGAAT AATTTATCTC GATGGGAAGA |
| 301 | AGAAAAAAAT GAAAGTATGA ATAAGATGG ATGATTGGAT AAACTAAAAG AGATGAAAAA |
| 361 | ATATATATAT AAATTATTAC AAAAAAAAAA AATCATACAA GAATGACATT ACTGAAGCAA |
| 421 | ATTCGCTTTC ACATGAAAAG TATGCAGTGT AAAGATATAA AAGTAAACCA TTATTTTGT |
| 481 | CACTAAAAAA TGGATACAGA AAACCGAACA TTAAAACATG ATCATTCATT CACCATTTTA |
| 541 | AAATTAAGAT GATTAATTTA AATAAAAAAA TCATATTAGA TAAGTGATCA AAATATTAGA |
| 601 | TAGTATAAAT TAATTCACGT AACATACACG CATTAATCGC GCTTCTTGAA TGATTAGTCA |
| 661 | GCAATTAAAC CGTGCTAATT TCTTTTCTCA CCTTCTAATC TTACCGCTGC CGGGAACGTG |
| 721 | TAAATTAAGT AGCATTGTAA AGCAGCTTTT TGGATTATAA ATATTATTAA ATATACTCAC |
| 781 | GGGTTGGGTA TAAATATTAA GATGGCCAGC ATTGGTTTCG CAGGGAGTTG CAGATAAACA |
| 841 | AAATCTAGCA GGAGCAAATT CACTTCTAAG ATACACATAT TAAGTTCACC AGAGAGAGAG |
| 901 | AGAGACATTA ATCAAGATGG GTACGTGGTT CACAAATGCA AGGCCGTATC TGCTGTTAGT |
| 961 | GGCGGTTCAA TTTGGCTCAG CAGGCATGTT CATATTTGCG ATGGATGCTA TAAAGAAGGG |
| 1021 | TATGAGCCAT TACGTGTTCA TCGTCTATCG TAATGCCATC GCCTCTGTAT CTCTTGCTCC |
| 1081 | CTTCGCATTC GTTTTAGAAA GGTCTCTTCC CCTTACTTCT CATCCATGCA TGCATATACA |
| 1141 | TCAAAGTGTA TATATATGTA TATATATATA TATTCACCTC TATTAAATTA AATTAAAAGA |
| 1201 | AATACTATTG TTTAATTTTG CAGGAAAATT AGGCCCAAGA TGACTTTCCG GGTATTTTCA |
| 1261 | GAG (SEQ ID NO:6) |

Figure 9

NEMATODE INFECTED:

| SeqID | Construct | Root tip | | Vascular | | Cortical | | Syncytia | |
|---|---|---|---|---|---|---|---|---|---|
| | | 7DAI | 12 DAI | 7DAI | 12 DAI | 7 DAI | 12 DAI | 7DAI | 12 DAI |
| 1 | pAW134qcz | - | - | ++ | ++ | - | - | ++ | ++ |
| 2 | pAW219qcz | - | + | ++ | ++ | - | - | - | + |
| 3 | pAW223qcz | - | - | ++ | ++ | - | - | + | + |

CONTROL UNINFECTED:

| SeqID | Construct | Root tip | Vascular | Cortical |
|---|---|---|---|---|
| 1 | pAW134qcz | - | ++ | - |
| 2 | pAW219qcz | - | ++ | - |
| 3 | pAW223qcz | - | + | - |

Figure 10

PROMOTER CONFIGURATION 1

| Element class | P$MADS | P$MYBS | P$DOFF |
|---|---|---|---|
| SEQ ID NO:1 location | 1714-1734 | 1733-1749 (- strand) | 1771-1787 |
| SEQ ID NO:3 location | 173-193 | 205-221 (- strand) | 214-230 |

PROMOTER CONFIGURATION 2

| Element class | P$OPAQ | P$AHPB | P$MADS | P$AHPB | P$TBPF |
|---|---|---|---|---|---|
| SEQ ID NO:1 location | 1506-1522 | 1543-1555 (- strand) | 1582-1602 | 1597-1609 | 1638-1652 |
| SEQ ID NO:3 location | 485-501 | 520-532 (- strand) | 574-594 | 635-647 | 660-674 |

PROMOTER CONFIGURATION 3

| Element class | P$TBPF | P$AHPB | P$MADS | P$DOFF | P$DOFF | P$AHPB |
|---|---|---|---|---|---|---|
| SEQ ID NO:1 location | 1638-1652 | 1697-1709 | 1714-1734 | 1771-1787 | 1825-1841 (- strand) | 1878-1890 |
| SEQ ID NO:3 location | 475-489 | 522-534 | 574-594 | 606-622 | 616-632 (- strand) | 635-647 |

Figure 11

| Common Primer | SEQ ID NO | Sequence 5' to 3' |
|---|---|---|
| At1g21890prF | 7 | CTGCAGCAGACAAAGAATTATTGGAAAACAATGAG |
| At1g21890prR | 8 | GGCGCGCCTTTATCTCTTTCTCTTTCTCTCTAAATTTCTC |
| At4g08290prF | 9 | CTGCAGCACTAATATAAGACATGGCACGTTTG |
| At4g08290prR2 | 10 | GGCGCGCCGGTTATTGAAATTTTGTGTTTATTTTTTTTTCTG |
| MtN21-2GW | 11 | GATAGGAAAGATGCCGACGTGAATTTCATGC |
| MtN21-2GWnest | 12 | CTCTGAAAATACCCGGAAAGTCATCTTGG |
| MtN21-2GW AP1 | 13 | GTAATACGACTCACTATAGGGC |
| MtN21-2GW AP2 | 14 | ACTATAGGGCACGCGTGGT |
| MtN21-3promFor | 15 | CTGCAGGGTTACAGTACCAATTCTG |
| MtN21-3promRev | 16 | GGCGCGCCCTTGATTAATGTCTCTCTCTC |
| pAW134pr650bpFor | 28 | CCAACTGCAGTGCTTTTTGATTCTTCGAAAC |
| pAW134pr442bpFor | 29 | ATGCCTGCAGCATTCTCATTAGTGATCGTAG |
| pAW134pr412bpFor | 30 | ATGCCTGCAGCTAGCCATCTTAATAAGC |
| pAW134pr365bpFor | 31 | ATGCCTGCAGATTTTACATACGCAAGTGTTC |
| pAW134pr315bpFor | 32 | ATGCCTGCAGTAAGTAGGTATGTAATATAAC |
| pAW134pr258bpFor | 33 | ATGCCTGCAGAGAACAAGACCATAGTTAG |
| pAW134prRev | 34 | GGACGTAACATGTCGAC |

Figure 12A

```
                              1                                                                          75
50444087          (1)   CACACAAGCAAATTCACTTCTCTGTTCTGACACACATATTAAGTTCCCGAGAAAGATCTAGAGAGTAATTAAGAT
50862200          (1)   ---------------------------------------------------------------------------
Consensus         (1)

76                                                                         150
50444087         (76)   GGGTACGTGGTTCACAAATGCAAGGCCGTATCTGCTGTTAGTGGCAGTTCAATTTGGGTCTGCTGGCATGTTCAT
50862200          (1)   ---------------------------------------------------------------------------
Consensus        (76)

151                                                                        225
50444087        (151)   ATTTGCGATGGATGCTATAAAGAAGGGTATGAGCCATTACGTGTTCATCGTCTATCGTAATGCCATCGCCTCTGT
50862200          (1)   ---------------------------------------------------------------------------
Consensus       (151)

226                                                                        300
50444087        (226)   ATCTCTTGCTCCCTTCGCATTTGTTCTTGAAAGGAAAGTTAGGCCCAAGATGACTTTCCGGGTATTTTCAGAGAT
50862200          (1)   ---------------------------------------------------------------------------
Consensus       (226)

301                                                                        375
50444087        (301)   TATGGCACTGGCTTTCTTCGAAATAATACTGGACCAGTGCTTCGCCCTCTTGGGCATGAAATTCACGTCGGCATC
50862200          (1)   ---------------------------------------------------------------------------
Consensus       (301)

376                                                                        450
50444087        (376)   TTTCCTATCTGCTGTTATGAACTCCGCTCCCTCTGTTACTTTTGTGATGGCTGTCATTCTAAGAATGGAGCACAT
50862200          (1)   ---------------------------------------------------------------------------
Consensus       (376)

451                                                                        525
50444087        (451)   GAAGATTAAGGAGGTGGCATGTCAAGCCAAAGTGATTGGCACAGTAATAACATTTGGAGGCACCTTGCTTATGGC
50862200          (1)   ---------------------------------------------------------------------------
Consensus       (451)

526                                                                        600
50444087        (526)   ACTGTACAAAGGACCCGTTCTTAGTTTTATGCGATCTTCAACTAGCCATCCTAGCCAACCTGAGAATGTGGCCAC
50862200          (1)   ---------------------------------------------------------------------------
Consensus       (526)

601                                                                        675
50444087        (601)   AGAAACTGGTAACCATTGGGTCATAGGGACATTGTTCCTCCTCATTGGTTGTGCTGGCTTTTCTGCATTTTACAT
50862200          (1)   ---------------------------------------------------------------------------
Consensus       (601)

676                                                                        750
50444087        (676)   ATTACAGGCCATAACATTGGAGAAATACCCAGCAGAGATGTCTCTGGCCACTTGGGTTTGCTTTGTAGGAGCACT
50862200          (1)   --------------------------------------------------------------------------T
Consensus       (676)                                                                                    T 751                                                                        825
50444087        (751)   TCAAAGCTCTATTGTTGCAATCTTCGCAGAACGCCACCACCCTCATGCTTGGTCCCTTGGTTGGGATACACGTCT
50862200          (2)   TCAAAGCTCTATTGTTGCAATCTTCGCAGAACGCCACCACCCTCATGCTTGGTCCCTTGGTTGGGATACACGACT
Consensus       (751)   TCAAAGCTCTATTGTTGCAATCTTCGCAGAACGCCACCACCCTCATGCTTGGTCCCTTGGTTGGGATACACG CT 826                                                                        900
50444087        (826)   CTTTGCTCCTGCTTACGCGGGAATAGTTACGTCTGGAGTTCAGTATTACATACAAGGCATGGTCTCAAAAATTAT
50862200         (77)   CTTTGCTCCTGCTTACGCGGGAATAGTTACATCTGGAGTTCAGTATTACATACAAGGCATGGTCTCAAAAATTAT
Consensus       (826)   CTTTGCTCCTGCTTACGCGGGAATAGTTAC TCTGGAGTTCAGTATTACATACAAGGCATGGTCTCAAAAATTAT 901                                                                        975
50444087        (901)   GGGCCCAGTTATTGTGACTGCTTTTAATCCCCTGCGTATGATCATTGTTACGGCCTTGGCCTGCATCATCTTATC
50862200        (152)   GGGCCCAGTTATTGTGACTGCTTTTAATCCCCTGCGTATGATCATTGTTACGGCCTTGGCCTGCATCATCTTATC
Consensus       (901)   GGGCCCAGTTATTGTGACTGCTTTTAATCCCCTGCGTATGATCATTGTTACGGCCTTGGCCTGCATCATCTTATC 976                                                                       1050
50444087        (976)   TGAACAACTCTTCCTTGGAAGTATTATTGGAGCAATAGTTGTGGTTCTTGGGCTTTATCTAGTTGTGTGGGGAAA
50862200        (227)   CGAGCAACTCTTCCTTGGAAGTATTATTGGAGCAGTAGTTGTGGTTCTTGGGCTTTATCTAGTTGTGTGGGGAAA
Consensus       (976)    GA CAACTCTTCCTTGGAAGTATTATTGGAGCA TAGTTGTGGTTCTTGGGCTTTATCTAGTTGTGTGGGGAAA
```

Figure 12B

```
                    1051                                                                      1125
50444087   (1051)   AGCTAAAGAACGTAGAGGTCTGATGACACCGTCCCCTGCAGAAAATAACTTTCCAGAAGACCAACGACAGCTACC
50862200   (302)    AGCTAAAGAACGCAGAGGTATTATGACACCGTCCCCTGCAGAAAATAACTTTCCGGAAGACCAACGACAGCTACC
Consensus  (1051)   AGCTAAAGAACG AGAGGT T ATGACACCGTCCCCTGCAGAAAATAACTTTCC GAAGACCAACGACAGCTACC 1126                                                                      1200
50444087   (1126)   GGTCACAGCTCCAAGGAATGATAGCATTAACAATAATAATAAGGCTTAATTAGTCCATCGCCATGATGAAAAAAG
50862200   (377)    AGTCATAGCTCCAAGGAATGATAACATT---AATACTAATAAGGCTTAATTAGTCCTTCGCCATGTTGAAAAAAC
Consensus  (1126)    GTCA AGCTCCAAGGAATGATA CATT   AATA TAATAAGGCTTAATTAGTCC TCGCCATG TGAAAAAA 1201                                                                      1275
50444087   (1201)   TGATGTGGAAGGCACAATATATCAAGAAGAGAAAGTCAGCAAAATTTAAGTAAAGGCCTCGGCTTTGTTTAATTA
50862200   (449)    TGATGTGGAAGGCACAATATATCAAGAAGAGAGAGTCAGTAAAATTTAAGTATAGGCCTAGGCTTTGTTTAATTA
Consensus  (1201)   TGATGTGGAAGGCACAATATATCAAGAAGAGA AGTCAG AAAATTTAAGTA AGGCCT GGCTTTGTTTAATTA 1276                                                                      1350
50444087   (1276)   GACATTGTTGTAGCATTCCATACAAATGATCTAAGGTCAATGTCATGCACATTACTAATACCATGAAATTGGTGG
50862200   (524)    GACATTGGTGTAGCATTCCGTACAAGTGATCTCAGGTCAATGTCATGCACATTACTAATACCATCAAATGGGTGG
Consensus  (1276)   GACATTG TGTAGCATTCC TACAA TGATCT AGGTCAATGTCATGCACATTACTAATACCATGAAAT GGTGG 1351                                                                      1425
50444087   (1351)   GATAAGTGGCATGACGATTGATGAAATTCATCATATATATAATTAATTAGTGGTCACTTTGAGCTGCAAAAAAA
50862200   (599)    GATAAGTGGCATGACGATTGGTGAAATTCATCATATATATAATTAATTAGTGATCAATTAGAGCTGCATCATTGT
Consensus  (1351)   GATAAGTGGCATGACGATTG TGAAATTCATCATATATATAATTAATTAGTG TCA TT GAGCTGCA  A 1426                                                                      1500
50444087   (1425)   -----AAAAAAAAAAA----------------------------------------------------------
50862200   (674)    TCTTGAGTTGAATGAACTAATGTGCTTCCGAGTCATCATAGAGTAATTATTTACACAGTTCTGGGCTAATTTGCT
Consensus  (1426)        A   AA AA 1501                                                                      1575
50444087   (1436)   ---------------------------------------------------------------------------
50862200   (749)    TTCATATTCCACTTTTAAGTATTCCAATTCAGGGCTATAAAAAAAATGTATTCCATTTAAGCTAAGGTTGGAGAT
Consensus  (1501)

1576                       1623
50444087   (1436)   ------------------------------------------------
50862200   (824)    TTTAATACAAGTCTAAACATATATTTTTAGCAAAAAAAAAAAAAAAAAA
Consensus  (1576)
```

Figure 13A

| SEQ ID NO:6 | b.#1 | ACTATAGGGC ACGCGTGGTC GACGGCCCGG GCTGGTATCA TAATTTTATT |
|---|---|---|
| SEQ ID NO:6 | b.#51 | TATTTATTTA TTTATTTTTG TGTCTCCATT CTATTGTAAA AATGAAATAA |
| SEQ ID NO:6 | b.#101 | TGTAAAACGA GTTTTGTTAT TTTATGGTTA CAGTACCAAT TCTGAAAAAA |
| SEQ ID NO:6 | b.#151 | CTTAATGTTT AGATAAACTT TTTTAAAAAA AATACTATTC GACTTGTTTA |
| SEQ ID NO:6 | b.#201 | AAGTTAATGA TATGAAATAA AATTTTCTAT GAATTACTTT TTGAGTAAAA |
| SEQ ID NO:6 | b.#251 | CCATATATGT GTACAGCAAA GTTTGAGAAT AATTTATCTC GATGGGAAGA |
| SEQ ID NO:6 | b.#301 | AGAAAAAAAT GAAAGTATGA ATAAGATGG ATGATTGGAT AAACTAAAAG |
| SEQ ID NO:6 | b.#351 | AGATGAAAAA ATATATATAT AAATTATTAC AAAAAAAAAA AATCATACAA |
| SEQ ID NO:6 | b.#401 | GAATGACATT ACTGAAGCAA ATTCGCTTTC ACATGAAAAG TATGCAGTGT |
| SEQ ID NO:6 | b.#451 | AAAGATATAA AAGTAAACCA TTATTTTTGT CACTAAAAAA TGGATACAGA |
| SEQ ID NO:6 | b.#501 | AAACCGAACA TTAAAACATG ATCATTCATT CACCATTTTA AAATTAAGAT |
| SEQ ID NO:6 | b.#551 | GATTAATTTA AATAAAAAAA TCATATTAGA TAAGTGATCA AAATATTAGA |
| SEQ ID NO:6 | b.#601 | TAGTATAAAT TAATTCACGT AACATACACG CATTAATCGC GCTTCTTGAA |
| SEQ ID NO:6 | b.#651 | TGATTAGTCA GCAATTAAAC CGTGCTAATT TCTTTTCTCA CCTTCTAATC |
| SEQ ID NO:6 | b.#701 | TTACCGCTGC CGGGAACGTG TAAATTAAGT AGCATTGTAA AGCAGCTTTT |
| SEQ ID NO:6 | b.#751 | TGGATTATAA ATATTATTAA ATATACTCAC GGGTTGGGTA TAAATATTAA |
| SEQ ID NO:4<br>SEQ ID NO:6 | b.>#1><br>b.#801 |                                                                                                                                                        CACA<br>GATGGCCAGC ATTGGTTTCG CAGGGAGTTG CAGATAAACA AAATCTAGCA |
| SEQ ID NO:4<br>SEQ ID NO:6 | b.#5<br>b.#851 | CAAGCAAATT CACTTCTCTG TTCTGACACA CATATTAAGT TCCCGAGAAA<br>GGAGCAAATT CACTTCT::: ::AAGATACA CATATTAAGT TCACCAGAGA |
| SEQ ID NO:4<br>SEQ ID NO:6 | b.#55<br>b.#901 | GATCTAGAGA G::TAATTAA GATGGGTACG TGGTTCACAA ATGCAAGGCC<br>GAGAGAGAGA CATTAATCAA GATGGGTACG TGGTTCACAA ATGCAAGGCC |
| SEQ ID NO:4<br>SEQ ID NO:6 | b.#105<br>b.#951 | GTATCTGCTG TTAGTGGCAG TTCAATTTGG GTCTGCTGGC ATGTTCATAT<br>GTATCTGCTG TTAGTGGCGG TTCAATTTGG CTCAGCAGGC ATGTTCATAT |
| SEQ ID NO:4<br>SEQ ID NO:6 | b.#155<br>b.#1001 | TTGCGATGGA TGCTATAAAG AAGGGTATGA GCCATTACGT GTTCATCGTC<br>TTGCGATGGA TGCTATAAAG AAGGGTATGA GCCATTACGT GTTCATCGTC |
| SEQ ID NO:4<br>SEQ ID NO:6 | b.#205<br>b.#1051 | TATCGTAATG CCATCGCCTC TGTATCTCTT GCTCCCTTCG CATTTGTTCT<br>TATCGTAATG CCATCGCCTC TGTATCTCTT GCTCCCTTCG CATTCGTTTT |

Figure 13B

```
                                                                                *   *
SEQ ID NO:4      b.#255        TGAAAG:::: :::::::::: :::::::::: :::::::::: ::::::::::
SEQ ID NO:6      b.#1101       AGAAAGGTCT CTTCCCCTTA CTTCTCATCC ATGCATGCAT ATACATCAAA
                               ..........  ..........  ..........  ..........  ..........
                                 *
SEQ ID NO:4      b.#305        :::::::::: :::::::::: :::::::::: :::::::::: ::::::::::
SEQ ID NO:6      b.#1151       GTGTATATAT ATGTATATAT ATATATATTC ACCTCTATTA AATTAAATTA
                               ..........  ..........  ..........  ..........  ..........

SEQ ID NO:4      b.#355        :::::::::: :::::::::: :::::::::GA AAGTTAGGCC CAAGATGACT
SEQ ID NO:6      b.#1201       AAAGAAATAC TATTGTTTAA TTTTGCAGGA AAATTAGGCC CAAGATGACT
                               ..........  ..........  ..........  ..........  ..........
                                                                 *
SEQ ID NO:4      b.#405        TTCCGGGTAT TTTCAGAGAT TATGGCACTG GCTTTCTTCG AAATAATACT
SEQ ID NO:6      b.#1251       TTCCGGGTAT TTTCAGAG
                               ..........  ..........  ..........  ..........  ..........

SEQ ID NO:4      b.#455        GGACCAGTGC TTCGCCCTCT TGGGCATGAA ATTCACGTCG GCATCTTTCC
                               ..........  ..........  ..........  ..........  ..........

SEQ ID NO:4      b.#505        TATCTGCTGT TATGAACTCC GCTCCCTCTG TTACTTTTGT GATGGCTGTC
                               ..........  ..........  ..........  ..........  ..........

SEQ ID NO:4      b.#555        ATTCTAAGAA TGGAGCACAT GAAGATTAAG GAGGTGGCAT GTCAAGCCAA
                               ..........  ..........  ..........  ..........  ..........

SEQ ID NO:4      b.#605        AGTGATTGGC ACAGTAATAA CATTTGGAGG CACCTTGCTT ATGGCACTGT
                               ..........  ..........  ..........  ..........  ..........

SEQ ID NO:4      b.#655        ACAAAGGACC CGTTCTTAGT TTTATGCGAT CTTCAACTAG CCATCCTAGC
                               ..........  ..........  ..........  ..........  ..........

SEQ ID NO:4      b.#705        CAACCTGAGA ATGTGGCCAC AGAAACTGGT AACCATTGGG TCATAGGGAC
                               ..........  ..........  ..........  ..........  ..........

SEQ ID NO:4      b.#755        ATTGTTCCTC CTCATTGGTT GTGCTGGCTT TTCTGCATTT TACATATTAC
                               ..........  ..........  ..........  ..........  ..........

SEQ ID NO:4      b.#805        AGGCCATAAC ATTGGAGAAA TACCCAGCAG AGATGTCTCT GGCCACTTGG
                               ..........  ..........  ..........  ..........  ..........

SEQ ID NO:4      b.#855        GTTTGCTTTG TAGGAGCACT TCAAAGCTCT ATTGTTGCAA TCTTCGCAGA
                               ..........  ..........  ..........  ..........  ..........

SEQ ID NO:4      b.#905        ACGCCACCAC CCTCATGCTT GGTCCCTTGG TTGGGATACA CGTCTCTTTG
                               ..........  ..........  ..........  ..........  ..........

SEQ ID NO:4      b.#955        CTCCTGCTTA CGCGGGAATA GTTACGTCTG GAGTTCAGTA TTACATACAA
                               ..........  ..........  ..........  ..........  ..........

SEQ ID NO:4      b.#1005       GGCATGGTCT CAAAAATTAT GGGCCCAGTT ATTGTGACTG CTTTTAATCC
                               ..........  ..........  ..........  ..........  ..........

SEQ ID NO:4      b.#1055       CCTGCGTATG ATCATTGTTA CGGCCTTGGC CTGCATCATC TTATCTGAAC
                               ..........  ..........  ..........  ..........  ..........

SEQ ID NO:4      b.#1105       AACTCTTCCT TGGAAGTATT ATTGGAGCAA TAGTTGTGGT TCTTGGGCTT
                               ..........  ..........  ..........  ..........  ..........

SEQ ID NO:4      b.#1155       TATCTAGTTG TGTGGGGAAA AGCTAAAGAA CGTAGAGGTC TGATGACACC
                               ..........  ..........  ..........  ..........  ..........

SEQ ID NO:4      b.#1205       GTCCCCTGCA GAAAATAACT TCCAGAAGA CCAACGACAG CTACCGGTCA
                               ..........  ..........  ..........  ..........  ..........

SEQ ID NO:4      b.#1255       CAGCTCCAAG GAATGATAGC ATTAACAATA ATAATAAGGC TTAATTAGTC
                               ..........  ..........  ..........  ..........  ..........
```

Figure 13C

```
SEQ ID NO:4   b.#1305    CATCGCCATG ATGAAAAAAG TGATGTGGAA GGCACAATAT ATCAAGAAGA
                         ..................................................

SEQ ID NO:4   b.#1355    GAAAGTCAGC AAAATTTAAG TAAAGGCCTC GGCTTTGTTT AATTAGACAT
                         ..................................................

SEQ ID NO:4   b.#1405    TGTTGTAGCA TTCCATACAA ATGATCTAAG GTCAATGTCA TGCACATTAC
                         ..................................................

SEQ ID NO:4   b.#1455    TAATACCATG AAATTGGTGG GATAAGTGGC ATGACCATTG ATGAAATTCA
                         ..................................................

SEQ ID NO:4   b.#1505    TCATATATAT AATTAATTAG TGGTCACTTT GAGCTGCAAA AAAAAAAAA
                         ..................................................

SEQ ID NO:4   b.#1555    AAAAAGCGGC CGC
                         ..................................................
```

Figure 14A

```
At1g21890pr650bp      11   ---------- ---------- ---------- TTCTTCGAAA CTATTTGGTT
At4g08290pr650bp     101   actggaaatc cgaagtcttt tccacgtcct TTCTGATGAA CATTTAACAT
Gm_MtN21pr650bp       28   ---------- ---------- ---------- ---------- ----------
                                                             ********** **********

At1g21890pr650bp      31   ATAACTTTCG GA-------- ---------- ---------- ----------
At4g08290pr650bp     151   AAAACGTTCG GActcttcgt gacacttaaa ccaaacatac acgtacgtag
Gm_MtN21pr650bp       28   ---------- ---------- ---------- ---------- ----------
                           ********** **

At1g21890pr650bp      43   ---------- ---------- ---------- ---------- ----------
At4g08290pr650bp     201   ctaacaatag acgtgtagat tttaggttta cgtgtttttc aagttgGGCA
Gm_MtN21pr650bp       28   ---------- ---------- ---------- ---------- ------GGGA
                                                                              ****
                                                                              ****

At1g21890pr650bp      43   ---------- ---------- ---------- ---------- ----------
At4g08290pr650bp     251   AGAACAAAAA AAaagagagc ctatgacctg tgcaacagga taatagtgtt
Gm_MtN21pr650bp       32   AGAAGAAAAA AAtg------ ---------- ---------- ----------
                           ********** **
                           ********** **

At1g21890pr650bp      43   ---------- ---------- ---------- ---------- ----------
At4g08290pr650bp     301   agcAAAAGAA ATCATCAGAG CCATTATATG ATAttgtttg cttttcaatt
Gm_MtN21pr650bp       46   ---AAAGTAT GAAATAAGAT GGATGATTGG ATAaactaaa agagatg---
                                ****** ********** ********** ***

.
                                       .
                                       .

At1g21890pr650bp      43   ---------- ---------- ---------- ---------- ----------
At4g08290pr650bp     401   ttgaacaaac gtatctcatt ggtcgtgtcc tAATAAATAA TTATATttca
Gm_MtN21pr650bp       90   ---------- ---------- ---------- -AAAAAATAT ATATATaaa-
                                                               ********** ******

At1g21890pr650bp      43   ---------- TATACTTA-- ---------- ---------- ----------
At4g08290pr650bp     451   tatacatgta TATACTTtat agttttttgtt tttccttttg ctactctaca
Gm_MtN21pr650bp      108   ---------- -----TTA-- ---------- ---------- ----------
                                       ********
                                         ***
                                         ***
                                         ***
                                         ***
                                         ***
```

Figure 14B

```
At1g21890pr650bp     51  ---------- --TAACAAAA AAAAAAAcct tcggatata catggttcgg
At4g08290pr650bp    601  tttcaataac ctTGACAGAA AAAAAAAATA AACACAAAAT TTCAATAacc
Gm_MtN21pr650bp     111  ---------- --TTACAAAA AAAAAAAATC ATACAAGAAT GACATTActg
                                       ||||||||| |||||||
                                       ********* ********** ********** *******
                                       ********* ********** ********** *******
                                       ********* ********** ********** *******
                                       ********* ********** ********** *******
                                       ********* *******
                                       ********* *******
                                       ********* *******
                                       ********* *******
                                       ********* *******
                                         ****** *******

At1g21890pr650bp     89  cttggacgta caggtctata taataatttg atatatattg gtacaTTTCA
At4g08290pr650bp    651  ---------- ---------- ---------- ---------- ----------
Gm_MtN21pr650bp     149  aagcaaattc gc-------- ---------- ---------- -----TTTCA
                                                                              *****

At1g21890pr650bp    139  TTTATATACT CTTTATTGGT ACGATACAt- ---------- ----------
At4g08290pr650bp    651  ---------- ---------- ---------- ---------- ----------
Gm_MtN21pr650bp     166  CATGAAAAGT ATGCAGTGTA AAGATATAaa agtaaaccat tattttttgtc
                         ********** ********** *******

.
                                      .
                                      .

At1g21890pr650bp    168  ---------- ---------- ---------- ---------- ----TTTGAT
At4g08290pr650bp    651  ---------- ---------- ---------- ---------- ----------
Gm_MtN21pr650bp     266  accatttttaa aattaagatg attaatttaa ataaaaaaat cataTTAGAT
                                                                              ******
                                                                              ******
                                                                              ******

At1g21890pr650bp    174  TCGTTATCAA TATATTAata ccacattgac gagaacattc tcattagtga
At4g08290pr650bp    651  ---------- ---------- ---------- ---------- ----------
Gm_MtN21pr650bp     316  AAGTGATCAA AATATTAgat ag-------- ---------- ----------
                         ********** *******
                         ********** *******
                         ********** *******

.
                                      .
                                      .

At1g21890pr650bp    324  aTATAAATTA ATTaagtagg tatgtaatat aaccaaggaa attacgatct
At4g08290pr650bp    651  ---------- ---------- ---------- ---------- ----------
Gm_MtN21pr650bp     338  -TATAAATTA ATTcacgtaa catacacgca ttaatcgcgc ttcttgaatg
                         ********* ***
                         ********* ***
                         ********* ***

.
                                      .
                                      .

At1g21890pr650bp    424  gatacgtgct tgaCAACAAT TAAAaaccta tattttta-- ----------
At4g08290pr650bp    651  ---------- ---------- ---------- ---------- ----------
Gm_MtN21pr650bp     393  ---------- ---CAGCAAT TAAAccgtgc taatttcttt tctcaccttc
                                         ******* ****
```

Figure 14C

```
At1g21890pr650bp    462  ---------- ---------A AAGTGATGCT TAAATAGCca atggattgaa
At4g08290pr650bp    651  ---------- ---------- ---------- ---------- ----------
Gm_MtN21pr650bp     430  taatcttacc gctgccgggA ACGTGTAAAT TAAGTAGCat tgtaaagca-
                                                *  ********** ********

At1g21890pr650bp    493  atgtgcactc gcatatattG CTTTTTGTGT CAGCACAATT TGGCTATATA
At4g08290pr650bp    651  ---------- ---------- ---------- ---------- ----------
Gm_MtN21pr650bp     479  ---------- ---------G CTTTTTGGAT TATAAATATT ATTAAATATA
                                                *  ********** ********** **********

At1g21890pr650bp    543  AGCAAGtact ctcttgtagt aatcattcac agtcataact aattaagtac
At4g08290pr650bp    651  ---------- ---------- ---------- ---------- ----------
Gm_MtN21pr650bp     510  CTCACGggtt gggtataaat attaagatgg ccagcattgg tttcgcaggg
                         ******

At1g21890pr650bp    593  ATTTGAATAC ATCAAATACC AAGAAAGAGA AATTTag--- ----------
At4g08290pr650bp    651  ---------- ---------- ---------- ---------- ----------
Gm_MtN21pr650bp     560  AGTTGCAGAT AAACAAAATC TAGCAGGAGC AAATTcactt ctaagataca
                         ********** ********** ********** *****

At1g21890pr650bp    630  ---------- -----AGAGA AAGAGAAAGA GATAAA---- -
At4g08290pr650bp    651  ---------- ---------- ---------- ---------- -
Gm_MtN21pr650bp     610  catattaagt tcaccAGAGA GAGAGAGAGA CATTAAtcaa g
                                          ***** ********** ******
                                          ***** ********** ******
                                          ***** ********** ******
```

Figure 15

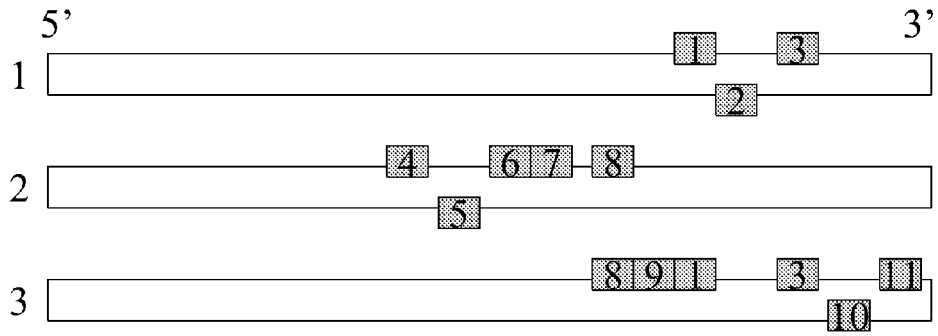

| Element # | In Promoter Configuration # | Element class descriptor | Element descriptor | Element IUPAC string consensus sequence |
|---|---|---|---|---|
| 1 | 1,3 | P$MADS | P$AGL2.01 | TNCCAWAWWTRGNAA (SEQ ID NO: 17) |
| 2 | 1 | P$MYBS (minus strand) | P$OSMYBS.01 | SWSKTATCCATNYM (SEQ ID NO: 18) |
| 3 | 1,3 | P$DOFF | P$PBF.01 | WNWAAAGNG (SEQ ID NO: 19) |
| 4 | 2 | P$OPAQ | P$O2.02 | CCACGT (SEQ ID NO: 20) |
| 5 | 2 | P$AHPB (minus strand) | P$WUS.01 | TTAATG (SEQ ID NO: 21) |
| 6 | 2 | P$MADS | P$MADSB.01 | WNCYAAAAATGSMAA (SEQ ID NO 22) |
| 7 | 2 | P$AHPB | P$ATHB1.01 | CAATTATT (SEQ ID NO: 23) |
| 8 | 2,3 | P$TBPF | P$TATA.01 | YNMTATAAATANA (SEQ ID NO: 24) |
| 9 | 3 | P$AHPB | P$ATHB9.01 | GTAATGATTRC (SEQ ID NO: 25) |
| 10 | 3 | P$DOFF (minus strand) | P$DOF2.01 | WAAAGC (SEQ ID NO: 26) |
| 11 | 3 | P$AHPB | P$ATHB9.01 | GTAATGATTRC (SEQ ID NO: 27) |

NEMATODE INDUCIBLE PLANT METABOLITE EXPORTER GENE PROMOTERS

RELATED APPLICATIONS

This application is a national stage application (under 35 U.S.C. 371) of PCT/EP2007/051378, filed Feb. 13, 2007, which claims benefit of U.S. Provisional application 60/743,341, filed Feb. 23, 2006.

SUBMISSION OF SEQUENCE LISTING

The Sequence Listing associated with this application is filed in electronic format via EFS-Web and hereby incorporated by reference into the specification in its entirety. The name of the text file containing the Sequence Listing is SequenceList__13156__00184_US. The size of the text file is 19 KB, and the text file was created on Aug. 19, 2008.

This invention relates to promoter sequences that regulate transcription of genes similar to *Medicago truncatula* Nodulin21 (MtN21). The promoters of MtN21-like genes of the invention are useful for controlling transcription of any nucleic acid of interest in plant roots. In particular, the promoters of the invention may be used to control transcription of nucleic acids that inhibit the reproduction of plant parasitic nematodes.

BACKGROUND OF THE INVENTION

Plant parasitic nematodes are microscopic wormlike animals that feed on the roots, leaves, and stems of more than 2,000 crops, vegetables, fruits, and ornamental plants, causing an estimated $100 billion crop loss worldwide. One common type of nematode is the root-knot nematode (RKN), whose feeding causes the characteristic galls on roots. Other root-feeding nematodes are the cyst- and lesion-types, which are more host specific.

Nematodes are present throughout the United States, but are mostly a problem in warm, humid areas of the South and West, and in sandy soils. Soybean cyst nematode (SCN), *Heterodera glycines*, was first discovered in the United States in North Carolina in 1954. It is the most serious pest of soybean plants. Some areas are so heavily infested by SCN that soybean production is no longer economically possible without control measures. Although soybean is the major economic crop attacked by SCN, SCN parasitizes some fifty hosts in total, including field crops, vegetables, ornamentals, and weeds.

Signs of nematode damage include stunting and yellowing of leaves, and wilting of the plants during hot periods. However, nematodes, including SCN, can cause significant yield loss without obvious above ground symptoms. In addition, roots infected with SCN are dwarfed or stunted. Nematode infestation can decrease the number of nitrogen-fixing nodules on the roots, and may make the roots more susceptible to attacks by other soil-borne plant pathogens.

The nematode life cycle has three major stages: egg, juvenile, and adult. The life cycle varies between species of nematodes. For example, the SCN life cycle can be completed in 24 to 30 days under optimum conditions, whereas other species can take as long as a year or more to complete the life cycle. When temperature and moisture levels become adequate in the spring, worm-shaped juveniles hatch from eggs in the soil. These juveniles are the only life stage of the nematode that can infect soybean roots.

The life cycle of SCN has been the subject of many studies and therefore can be used as an example for understanding the nematode life cycle. After penetrating the soybean roots, SCN juveniles move through the root until they contact vascular tissue, where they stop and start to feed. The nematode injects secretions that modify certain root cells and transform them into specialized feeding sites. The root cells are morphologically transformed into large multinucleate syncytia (or giant cells in the case of RKN), which are used as a source of nutrients for the nematodes. The actively feeding nematodes thus steal essential nutrients from the plant resulting in yield loss. As the nematodes feed, they swell and eventually female nematodes become so large that they break through the root tissue and are exposed on the surface of the root.

After a period of feeding, male SCN nematodes, which are not swollen as adults, migrate out of the root into the soil and fertilize the lemon-shaped adult females. The males then die, while the females remain attached to the root system and continue to feed. The eggs in the swollen females begin developing, initially in a mass or egg sac outside the body, then later within the body cavity. Eventually the entire body cavity of the adult female is filled with eggs, and the female nematode dies. It is the egg-filled body of the dead female that is referred to as the cyst. Cysts eventually dislodge and are found free in the soil. The walls of the cyst become very tough, providing excellent protection for the approximately 200 to 400 eggs contained within. SCN eggs survive within the cyst until proper hatching conditions occur. Although many of the eggs may hatch within the first year, many also will survive within the cysts for several years.

A nematode can move through the soil only a few inches per year on its own. However, nematode infestation can be spread over substantial distances in a variety of ways. Anything that can move infested soil is capable of spreading the infestation, including farm machinery, vehicles and tools, wind, water, animals, and farm workers. Seed-sized particles of soil often contaminate harvested seed. Consequently, nematode infestation can be spread when contaminated seed from infested fields is planted in non-infested fields. There is even evidence that certain nematode species can be spread by birds. Unfortunately, only some of these causes can be prevented.

Traditional practices for managing nematode infestation include: maintaining proper soil nutrients and soil pH levels in nematode-infested land; controlling other plant diseases, as well as insect and weed pests; using sanitation practices such as plowing, planting, and cultivating of SCN-infested fields only after working in non-infested fields; cleaning equipment thoroughly with high pressure water or steam after working in infested fields; not using seed grown on infested land for planting non-infested fields unless the seed has been properly cleaned; rotating infested fields and alternating host crops with non-host crops; using nematicides; and planting resistant plant varieties.

Methods have been proposed for the genetic transformation of plants in order to confer increased resistance to plant parasitic nematodes. U.S. Pat. Nos. 5,589,622 and 5,824,876 are directed to the identification of plant genes expressed specifically in or adjacent to the feeding site of the plant after attachment by the nematode. U.S. Pat. Nos. 5,589,622 and 5,824,876 disclose eight promoters isolated from potato roots infected with *Globodera rostochiensis*: no nematode-inducible promoters from other plant species are disclosed. These promoters are purported to be useful to direct the specific expression of toxic proteins or enzymes, or the expression of antisense RNA to a target gene or to general cellular genes.

U.S. Pat. No. 5,023,179 discloses a promoter enhancer element designated ASF-1, isolated from the CaMV promoter, which is purported to enhance plant gene expression in roots.

U.S. Pat. No. 5,750,386 discloses a deletion fragment of the RB7 root specific promoter of *Nicotiana tabacum*, which is purported to be nematode-responsive.

U.S. Pat. No. 5,837,876 discloses a root cortex specific gene promoter isolated from tobacco and designated TobRD2.

U.S. Pat. No. 5,866,777 discloses a two-gene approach to retarding formation of a nematode feeding structure. The first gene, barnase, is under control of a promoter that drives expression at least in the feeding structure. The second gene, barstar, is under control of a promoter that drives expression in all of the plant's cells except the feeding structure. Feeding site-specific promoters disclosed in U.S. Pat. No. 5,866,777 include truncated versions of the Δ0.3TobRB7 and roIC promoters.

U.S. Pat. No. 5,955,646 discloses chimeric regulatory regions based on promoters derived from the mannopine synthase and octopine synthase genes of *Agrobacterium tumefaciens*, which are purported to be nematode-inducible.

U.S. Pat. No. 6,005,092 discloses the *N. tabacum* endo-1, 4-β-glucanase (Ntce17) promoter.

U.S. Pat. Nos. 6,262,344 and 6,395,963 disclose promoters isolated from *Arabidopsis thaliana*, which are purported to be nematode-inducible.

U.S. Pat. No. 6,448,471 discloses a promoter from *A. thaliana*, which is specific for nematode feeding sites.

U.S. Pat. No. 6,593,513 discloses transformation of plants with barnase under control of the promoter of the *A. thaliana* endo-1,4-β-glucanase gene (cell) to produce plants capable of disrupting nematode attack.

U.S. Pat. No. 6,906,241 discloses use of the Ntce17 promoter in combination with a heterologous nucleic acid that encodes a nematocidal or insecticidal protein.

U.S. Pat. No. 7,078,589 discloses cloning and isolation of the soybean Pyk20 gene and promoter, which are purported to be induced by SCN infection and to show strong activity in vascular tissues.

U.S. Patent Application Publication No. 2003/0167507 discloses the promoter of soybean isoflavone synthase I, which is purported to be root specific and inducible in vegetative tissue by parasite attack.

U.S. Patent Application Publication No. 2004/0078841 discloses promoter regions of the TUB-1, RPL16A, and ARSK1 promoters of *Arabidopsis thaliana* and the PSMT$_A$ promoter from *Pisum sativum*, all of which are purported to be root-specific.

U.S. Patent Application Publication No. 2004/0248304 discloses cloning and isolation of the soybean Pyk20 gene and promoter, which are purported to be induced by SCN infection and to show strong activity in vascular tissues.

U.S. Patent Application Publication No. 2004/0029167 discloses a promoter sequence of a class II caffeic acid O-methyltransferase gene from tobacco, which is purported to be inducible in response to mechanical or chemical injury or to aggression by a pathogenic agent.

U.S. Patent Application Publication No. 2005/0262585 discloses a promoter from soybean phosphoribosylformylglycinamidine ribonucleotide synthase and deletion fragments thereof, which are purported to be responsive to nematode infection.

WO 94/10320 discloses the Δ0.3TobRB7 promoter fragment from tobacco and its use with a variety of genes for nematode feeding cell-specific expression.

WO 03/033651 discloses synthetic nematode-regulated promoter sequences designated SCP1, UCP3, and SUP.

WO 2004/029222 and its US counterpart U.S. Patent Application Publication No. 2005/0070697 disclose regulatory regions from the soybean adenosine-5'-phosphate deaminase and inositol-5-phosphatase genes, for use in improving nematode resistance in plants.

None of the above-mentioned root- or feeding-site specific promoters are currently in use in commercial seed containing an anti-nematode transgene. Although the need for such products has long been acknowledged, no one has thus far succeeded in developing nematode-resistant plants through recombinant DNA technology. A need continues to exist for root-specific and/or nematode feeding site-specific promoters to combine with transgenes encoding agents toxic to plant parasitic nematodes.

SUMMARY OF THE INVENTION

The present inventors have discovered that when plant gene promoters comprise certain known regulatory elements in specific orientation to each other, the promoters share the characteristics of being inducible by nematodes. Accordingly, the invention provides promoters suitable for use in driving expression of a second nucleic acid in plant roots, which are susceptible to attack by nematodes. The promoters of the invention are particularly useful for making agricultural crop plants resistant to infestation by nematodes.

In one embodiment, the invention provides an isolated nucleic acid of Promoter Configuration 1 wherein the nucleic acid has a plus strand and a minus strand, and comprises, in combination and in 5' to 3' order, a P$MADS class element on the plus strand, a P$MYBS class element on the minus strand, and a P$DOFF class element on the plus strand, wherein the P$MADS class element is within about 50 nucleotides of the P$MYBS class element, the P$MYBS class element is within about 50 nucleotides of the P$DOFF class element, and the P$MADS class element is within about 100 nucleotides of the P$DOFF class element.

In another embodiment, the invention provides an isolated nucleic acid of Promoter Configuration 2, wherein the nucleic acid has a plus strand and a minus strand, and comprises, in combination and in 5' to 3' order, a P$OPAQ class element on the plus strand, a first P$AHPB class element on the minus strand, a P$MADS class element on the plus strand, a second P$AHPB class element on the plus strand, and a P$TBPF class element on the plus strand, wherein the P$OPAQ class element is within about 60 nucleotides of the first P$AHPB class element, the first P$AHPB class element is within about 60 nucleotides of the P$MADS class element, the P$MADS class element is within about 60 nucleotides of the second P$AHPB class element, the second P$AHPB class element is within about 60 nucleotides of the P$TBPF class element and the P$OPAQ class element is within about 240 nucleotides of the P$TBPF class element.

In another embodiment the invention provides an isolated nucleic acid of Promoter Configuration 3, wherein the nucleic acid has a plus strand and a minus strand, and comprises, in combination and in 5' to 3' order, a P$TBPF class element on the plus strand, a first P$AHPB class element on the plus strand, a P$MADS class element on the plus strand, a first P$DOFF class element on the plus strand, a second P$DOFF class element on the minus strand, and a second P$AHPB class element on the plus strand, wherein the P$TBPF class element is within about 60 nucleotides of the first P$AHPB class element, the first P$AHPB class element is within about 60 nucleotides of the P$MADS class element, the P$MADS class element is within about 60 nucleotides of the first P$DOFF class element, the first P$DOFF class element is within about 60 nucleotides of the second P$DOFF class element, the second P$DOFF class element is within about 60 nucleotides of the second P$AHPB class element and the P$TBPF class element is within about 300 nucleotides of the second P$AHPB class element.

In another embodiment, the invention provides a promoter comprising an isolated nucleic acid selected from the group consisting of a nucleic acid having a sequence as set forth in SEQ ID NO:1; a nucleic acid that hybridizes under stringent conditions to a nucleic acid having a sequence as set forth in SEQ ID NO:1; a nucleic acid comprising nucleotides 1554 to 1887 of a sequence as set forth in SEQ ID NO:1; a nucleic acid that hybridizes under stringent conditions to a nucleic acid comprising nucleotides 1554 to 1887 of a sequence as set forth in SEQ ID NO:1; a nucleic acid having a sequence as set forth in SEQ ID NO:2; a nucleic acid that hybridizes under stringent conditions to a nucleic acid having a sequence as set forth in SEQ ID NO:2; a nucleic acid comprising nucleotides 1569 to 1902 of a sequence as set forth in SEQ ID NO:2; a nucleic acid that hybridizes under stringent conditions to a nucleic acid comprising nucleotides 1569 to 1902 of a sequence as set forth in SEQ ID NO:2; a nucleic acid having a sequence as set forth in SEQ ID NO:3; a nucleic acid that hybridizes under stringent conditions to a nucleic acid having a sequence as set forth in SEQ ID NO:3; a nucleic acid comprising nucleotides 364 to 697 of a sequence as set forth in SEQ ID NO:3; and a nucleic acid that hybridizes under stringent conditions to a nucleic acid comprising nucleotides 364 to 697 of a sequence as set forth in SEQ ID NO:3.

The invention is also embodied in expression cassettes and transgenic plants which comprise the promoters of the invention, and in methods of controlling infestation of crops by parasitic nematodes, wherein the methods employ recombinant nucleic acid constructs comprising the promoters of the invention in operative association with a second nucleic acid that encodes an agent toxic to plant parasitic nematodes.

BRIEF DESCRIPTION OF THE DRAWINGS

FIG. 1A: Sequence of *Arabidopsis thaliana* promoter region of locus At1g21890 (SEQ ID NO:1), the TATA box at bases 1854-1860 is in lower case, bold, and italic; FIG. 1B is a table of promoter element classes present in Promoter Configuration 1, Promoter Configuration 2, and Promoter Configuration 3 which are contained within the promoter set forth in SEQ ID NO:1.

FIG. 2: Sequence of *A. thaliana* promoter region of locus At4g08290 (SEQ ID NO:2) the TATA box at bases 1869-1875 is in bold.

FIG. 3: Sequence of promoter region of *Glycine max* MtN21-3 (SEQ ID NO:3), the TATA box at bases 664-670 is part of lower case and is in bold and underlined. Also included in FIG. 3 is a table of promoter element classes present in Promoter Configuration 1, Promoter Configuration 2, and Promoter Configuration 3 which are contained within the promoter set forth in SEQ ID NO:3.

FIG. 4: cDNA sequences of GmMtN21-2 (GM50444087; SEQ ID NO:4) and GmMtN21-1 (GM50862200, SEQ ID NO:5).

FIG. 5: Sequence of GmMtN21-3 (SEQ ID NO:6).

FIG. 9: β-glucuronidase expression patterns of binary vectors pAW134qcz, pAW219qcz, and pAW223qcz in the soybean hairy root assay set forth in Example 3. "DAI" means days after inoculation with SCN. The following scoring index was used: "−" for no GUS staining, "+" for GUS weak staining, "++" for strong GUS staining. A round-up average of the 10 counts was used to determine the GUS expression level in the syncytia for that line. In addition, GUS expression level in the same lines for other root tissues such as callus, root-tip, vasculature, cortical and primordial were also recorded using the same GUS scoring index of "−" for no staining, "+" for weak staining, "++" for strong staining.

FIG. 10: Locations of promoter element classes of Promoter Configuration 1, Promoter Configuration 2, and Promoter Configuration 3 in the *A. thaliana* promoter of locus At1g21890 (SEQ ID NO:1) and the *G. max* MtN21-3 promoter (SEQ ID NO:3).

FIG. 11: PCR primers used to obtain the promoters of SEQ ID NO:1, SEQ ID NO:2, and SEQ ID NO:3, and the deletions of SEQ ID NO:1 in Example 7.

FIG. 12A-12B: Sequence alignment of soybean cDNAs GmMtN21-2 (GM50444087; SEQ ID NO:4) and GmMtN21-1 (GM50862200, SEQ ID NO:5).

FIG. 13A, 13B, 13C: Sequence alignment of genome walking fragment GmMtN21-3 (SEQ ID NO:6) and soybean cDNA GmMtN21-2 (GM50444087; SEQ ID NO:4). The ATG start codon of GmMtN21-2 (SEQ ID NO:4) starts at bp 74. A putative promoter region of 793 bp is described by SEQ ID NO:3 and is derived from bases 126 to 916 of GmMtN21-3 (SEQ ID NO:6).

FIG. 14A, 14B, 14C: Genomatix DiAlign results comparing bases 1318 to 1967 of SEQ ID NO:1 (corresponding to bases 1 to 650 of At1g21890pr650 bp), bases 1298 to 1947 of SEQ ID NO:2 (corresponding to bases 1 to 650 of At4g08290pr650 bp), and bases 142 to 791 of SEQ ID NO:3 (corresponding to bases 1 to 650 of Gm_MtN21 pr650 bp).

FIG. 15: Spatial configuration of promoter element classes found in Promoter Configuration 1, Promoter Configuration 2, and Promoter Configuration 3 (not to exact scale) including promoter element class consensus sequences. In the column entitled "Element IUPAC string consensus sequence," the following abbreviations are employed: A=adenine, C=cytosine, G=guanine, T=thymine, R=A or G, Y=C or T, M=A or C, K=G or T, W=A or T, S=C or G, and N=A, C, G, or T. Key to the configurations is as follows:
1: Representation of promoter element classes contained in bases 1318 to 1967 of SEQ ID NO:1 comprising Promoter Configuration 1.
2: Representation of promoter element classes contained in bases 1318 to 1967 of SEQ ID NO:1 comprising Promoter Configuration 2.
3: Representation of promoter element classes contained in bases 1318 to 1967 of SEQ ID NO:1 comprising Promoter Configuration 3.

Figure 6:
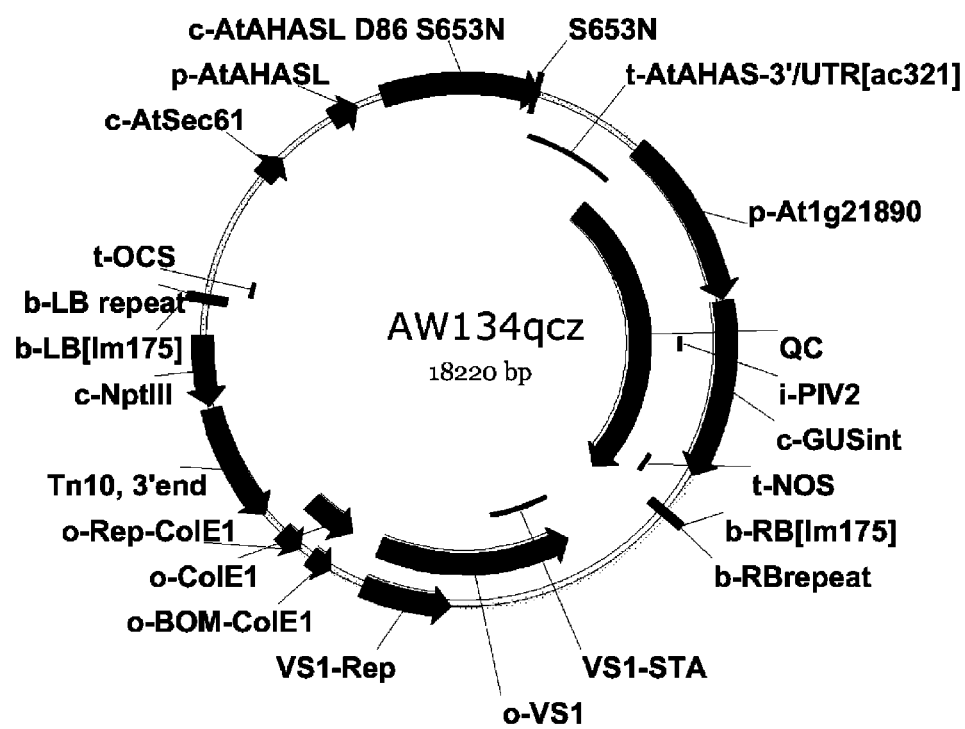
FIG. 6: Map of binary vector pAW134qcz containing the *A. thaliana* promoter of locus At1g21890 (SEQ ID NO:1)

A round-up average of the 10 counts was used to determine the GUS expression level in the syncytia for each line.

DETAILED DESCRIPTION OF PREFERRED EMBODIMENTS

The present invention may be understood more readily by reference to the following detailed description of the preferred embodiments of the invention and the examples included herein. Unless otherwise noted, the terms used herein are to be understood according to conventional usage by those of ordinary skill in the relevant art. In addition to the definitions of terms provided below, definitions of common terms in molecular biology may also be found in Rieger et al, 1991 Glossary of genetics: classical and molecular, 5$^{th}$ Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that this invention is not limited to specific nucleic acids, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook and Russell, 2001 Molecular Cloning, Third Edition, Cold Spring Harbor, Plainview, N.Y.; Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York.

The promoters of the invention are isolated nucleic acids. An "isolated" nucleic acid as used herein is substantially free of other cellular materials or culture medium when produced by recombinant techniques, or substantially free of chemical precursors when chemically synthesized. Further more, the isolated nucleic acids of the invention are substantially free of flanking (i.e., sequences located 5' or 3' thereof) present in the native genome of the organism from which the nucleic acid is derived.

In accordance with the invention, the promoters of the present invention may be placed in operative association with a second nucleic acid for root-specific and/or nematode-inducible expression of the second nucleic acid in plants in order to vary the phenotype of that plant. As used herein, the terms "in operative association," "operably linked," and "associated with" are interchangeable and mean the functional linkage of a promoter and a second nucleic acid sequence on a single nucleic acid fragment in such a way that the transcription of the second nucleic acid is initiated and mediated by the promoter. In general, nucleic acids which are in operative association are contiguous.

Second nucleic acid sequences include, for example, an open reading frame, a portion of an open reading frame, a nucleic acid encoding a fusion protein, an anti-sense sequence, a sequence encoding a double-stranded RNA sequence, a transgene, and the like. For example, the second nucleic acid may encode an insect resistance gene, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker gene, a positive selectable marker gene, a gene affecting plant agronomic characteristics (i.e., yield), an environmental stress resistance gene (as exemplified by genes imparting resistance or tolerance to drought, heat, chilling, freezing, excessive moisture, salt stress, or oxidative stress), genes which improve starch properties or quantity, oil quantity and quality, amino acid or protein composition, and the like.

Preferably, the second nucleic acid encodes a double-stranded RNA or antisense nucleic acid which is substantially identical or homologous in whole or in part to a plant gene required for formation or maintenance of a feeding site. The second nucleic acid may alternatively encode an agent that disrupts the growth, development, and/or reproduction of the plant parasitic nematodes ("nematode-toxic") to reduce crop destruction. Any nucleic acid encoding a nematode-toxic agent to plant parasitic nematodes may be employed in accordance with the invention. For example, the nematode-toxic second nucleic acid may encode a double stranded RNA which is substantially identical to a target gene of a parasitic plant nematode which is essential for survival, metamorphosis, or reproduction of the nematode. As used herein, taking into consideration the substitution of uracil for thymine when comparing RNA and DNA sequences, the terms "substantially identical" and "corresponding to" mean that the nucleotide sequence of one strand of the dsRNA is at least about 80%-90% identical to 20 or more contiguous nucleotides of the target gene, more preferably, at least about 90-95% identical to 20 or more contiguous nucleotides of the target gene, and most preferably at least about 95-99% identical or absolutely identical to 20 or more contiguous nucleotides of the target gene. Exemplary plant parasitic nematode target genes are set forth, for example, in commonly assigned copending US Patent Application Publication Number 2005/188438, incorporated herein by reference. The second nucleic acid may alternatively encode a double stranded RNA, which is substantially identical to a plant gene required to maintain a nematode feeding site Alternatively, for nematode control, the second nucleic acid placed in operative association with the promoters of the invention may encode a nematode-toxic protein. For example, nucleic acids encoding microbial toxins or fragments thereof, toxins or fragments thereof derived from insects such as those described in U.S. Pat. Nos. 5,457,178; 5,695,954; 5,763,568; 5,959,182; and the like, are useful in this embodiment of the invention.

Crop plants and corresponding pathogenic nematodes are listed in Index of Plant Diseases in the United States (U.S. Dept. of Agriculture Handbook No. 165, 1960); Distribution of Plant-Parasitic Nematode Species in North America (Society of Nematologists, 1985); and Fungi on Plants and Plant Products in the United States (American Phytopathological Society, 1989). For example, plant parasitic nematodes which are targeted by the present invention include, without limitation, cyst nematodes and root-knot nematodes. Specific plant parasitic nematodes which are targeted by the present invention include, without limitation, *Heterodera glycines, Heterodera schachtii, Heterodera avenae, Heterodera oryzae, Heterodera cajani, Heterodera trifolii, Globodera pallida, G. rostochiensis*, or *Globodera tabacum, Meloidogyne incognita, M. arenaria, M. hapla, M. javanica, M. naasi, M. exigua, Ditylenchus dipsaci, Ditylenchus angustus, Radopholus similis, Radopholus citrophilus, Helicotylenchus multicinctus, Pratylenchus coffeae, Pratylenchus brachyurus, Pratylenchus vulnus, Paratylenchus curvitatus, Paratylenchus zeae, Rotylenchulus reniformis, Paratrichodorus anemones, Paratrichodorus minor, Paratrichodorus christiei, Anguina tritici, Bidera avenae, Subanguina radicicola, Hoplolaimus seinhorsti, Hoplolaimus Columbus, Hoplolaimus galeatus, Tylenchulus semipenetrans, Hemicycliophora arenaria, Rhadinaphelenchus cocophilus, Belonolaimus longicaudatus, Trichodorus primitivus, Nacoabbus aberrans, Aphelenchiodes besseyi, Hemicriconemoides kanayaensis, Tylenchorhynchus claytoni, Xiphinema americanum, Cacopaurus pestis*, and the like.

Crops which may be protected by nucleic acid constructs containing the promoters of the present invention include, without limitation, soybean (*G. max*), potato (*Solanum tuberosum*), peanuts (*Arachis hypogaea*), cotton (*Gossypium hirsutum*), cassaya (*Manihot esculenta*), coffee (*Cofea* spp.), coconut (*Cocos nucifera*), pineapple (*Ananas comosus*), citrus trees (*Citrus* spp.), banana (*Musa* spp.), corn (*Zea mays*), rape—including canola (*Brassica* spp.), sunflower, sorghum, wheat, oats, rye, barley, rice, beets—including sugar beets, and vegetables such as green beans (*Phaseolus vulgaris*), lima beans (*Phaseolus limensis*), and peas (*Lathyrus* spp.), tobacco (*Nicotiana tabacum*), and the like.

Commonly assigned U.S. patent application entitled "MtN21-like Gene Induced by Nematodes," U.S. Ser. No. 60/743,340, filed on the same date as U.S. Ser. No. 60/743, 341, both of which are incorporated herein by reference, discloses and claims a soybean gene designated *Glycine max* MtN-21, which is induced in feeding cells formed after nematode infection (See SEQ ID NOs: 4-6). The *Arabidopsis* promoters of the invention (SEQ ID NOs:1 and 2) represent promoter regions of *Arabidopsis* orthologs of the soybean MtN-21 coding sequence and were isolated from *Arabidopsis* genomic DNA as disclosed in Example 1. The soybean MtN-21 promoter of this invention (SEQ ID NO:3) was isolated from soybean genomic DNA as disclosed in Example 2. As demonstrated in Example 3, when placed in operative association with a GUS reporter gene, the *Arabidopsis* and soybean promoters of the invention are upregulated in soybean hairy roots infected by nematodes.

The invention is thus embodied in a promoter comprising an isolated nucleic acid sequence as set forth in SEQ ID NO:1, SEQ ID NO:2, or SEQ ID NO:3, or minimal promoter fragments of SEQ ID NO:1, SEQ ID NO:2, or SEQ ID NO:3 which are capable of driving root-specific and/or nematode-inducible expression of a second nucleic acid. Specific minimal promoter fragments of the invention include, without limitation, a nucleic acid comprising nucleotides 1554 to 1887 of a sequence as set forth in SEQ ID NO:1; a nucleic acid comprising nucleotides 1569 to 1902 of a sequence as set forth in SEQ ID NO:2; and a nucleic acid comprising nucleotides 364 to 697 of a sequence as set forth in SEQ ID NO:3. The methods disclosed herein may be employed to isolate additional minimal fragments of SEQ ID NO:1, SEQ ID NO:2, and SEQ ID NO:3 which are capable of mediating root-specific and/or nematode-inducible expression of a second nucleic acid.

Alternatively, the promoter of the invention comprises an isolated nucleic acid which hybridizes under stringent conditions to a nucleic acid having a sequence as set forth in SEQ ID NO:1, SEQ ID NO:2, or SEQ ID NO:3. Stringent hybridization conditions as used herein are well known, including, for example, 400 mM NaCl, 40 mM PIPES pH 6.4, 1 mM EDTA, 60° C. hybridization for 12-16 hours; followed by washing in 0.1SSC and 0.1% SDS at approximately 65° C. for about 15-60 minutes. The invention is further embodied in an isolated nucleic acid that hybridizes under stringent conditions to a nucleic acid comprising nucleotides 1554 to 1887 of a sequence as set forth in SEQ ID NO:1; a nucleic acid that hybridizes under stringent conditions to a nucleic acid comprising nucleotides 1569 to 1902 of a sequence as set forth in SEQ ID NO:2; and a nucleic acid that hybridizes under stringent conditions to a nucleic acid comprising nucleotides 364 to 697 of a sequence as set forth in SEQ ID NO:3.

In addition to promoters comprising the specific isolated sequences set forth in SEQ ID NOs:1-3 and the minimal promoter regions contained therein, and promoters which hybridize under stringent conditions to promoters comprising the specific sequences set forth in SEQ ID NOs;1-3, the present invention encompasses any isolated nucleic acid of Promoter Configuration 1, Promoter Configuration 2, and Promoter Configuration 3 described herein. The term "Promoter Configuration" is used here to describe a specific combination of multiple promoter element classes arranged in the 5' to 3' direction within a promoter sequence, wherein each promoter element class is in a specific spatial orientation to each other promoter element class. Promoter elements can be identified in numerous ways familiar to one of skill in the art. One such method utilizes the Genomatix CoreSearch™ algorithm (Genomatix Software GmbH, Munich, Germany). The CoreSearch naming convention utilizes "P" to denote a plant based promoter element and a "U" to identify a user defined promoter element. These broad identifiers are separated from the element type by a "$". The element class follows the "$"; for example, "OPAQ", "MADS", or MYBS".

As indicated in FIG. 15, the P$MADS promoter element class is designated as "Element 1" and exemplified by the element descriptor P$AGL2.01, which has the consensus sequence TNCCAWAWWTRGNAA (SEQ ID NO:17), see Huang H., et al. (1996) Plant Cell 8: 81-94. The P$MYBS promoter element class indicated in FIG. 15 as "Element 2" is exemplified by the element descriptor P$OSMYBS.01, which has the consensus sequence SWSKTATCCATNYM (SEQ ID NO:18), see Toyofuku K., et al. (1998) FEBS Lett. 428:275-280; Morita A., et al. (1998) FEBS Lett. 423:81-85; Gubler F., et al. (1992) Plant Cell 4:1435-1441; Lanahan M. B., et al. (1992) Plant Cell 4:203-211; Huttly A. K., et al. Mol. Gen. Genet. (1988) 214:232-240; Isabel-LaMoneda I., et al. (2003) Plant J. 33:329-340; and Lu C. A., et al. (2002) Plant Cell 14:1963-1980. The P$DOFF promoter element class exemplified by the element descriptor P$PBF.01, which has the consensus sequence WNWAAAGNG (SEQ ID NO:19) and is indicated in FIG. 15 as "Element 3", see Yanagisawa S., et al. Plant J. 17:209-214 (1999). The P$OPAQ promoter element class exemplified by the element descriptor P$O2.02, which has the consensus sequence CCACGT (SEQ ID NO:20) and is designated in FIG. 15 as "Element 4", see Cord Neto G., et al (1995) Plant. Mol. Biol. 27:1015-1029; Vincentz M., et al. (1997) Plant. Mol. Biol. 34:879-889; Hwang Y. S., et al. (2004) Plant Cell Physiol. 45:1509-1518. The P$AHPB element class is exemplified by the element descriptor P$WUS.01, which has the consensus sequence TTMTG (SEQ ID NO:21), and is designated in FIG. 15 as "Element 5," see Hong R. L., et al. (2003) Plant Cell 15:1296-1309; Lohmann J. U., et al. (2001) Cell 105:793-803. The P$MADS element class is exemplified by the element descriptor P$MADSB.01, which has the consensus sequence WNCYAAAAATGSMAA (SEQ ID NO:22), and is designated "Element 6" in FIG. 15, see Riechmann J. L., et al. (1996) Nucleic Acids Res. 24:3134-3141; Hill T. A., et al. (1998) Development 125:1711-1721. The P$AHPB element class is exemplified by the element descriptor P$ATHB1.01, which has the consensus sequence CAATTATT (SEQ ID NO:23), and is designated in FIG. 15 as "Element 7," see Sessa G., et al. (1993) EMBO J. 12:3507-3517. The P$TBPF element class is exemplified by the P$TATA.01 element descriptor, which has the consensus sequence YNMTATAAATANA (SEQ ID NO:24), and is designated in FIG. 15 as "Element 8" see Gidoni D., et al. (1989) Mol. Gen. Genet. 215:337-344; Yang H., et al. (2000) Plant Mol. Biol. 44:635-647; Chiron H., et al. (2000) Plant Physiol. 124:865-872; Guerineau F., et al. (2003) J. Exp. Bot. 54:1153-1162; Haralampidis K., et al. (2002) Plant Physiol. 129:1138-1149; Ishizaka T., et al. (2003) Genes Genet. Syst. 78:191-194; Hasegawa K., et al. (2003) Plant J. 33:1063-1072. The P$AHPB element class is exemplified by the P$ATHB9.01 element descriptor, which has the consensus sequence GTAATGATTRC (SEQ ID NO:25), and is designated as "Element 9" in FIG. 15, see Sessa G., et al. (1998) Plant Mol. Biol. 38:609-622. The P$DOFF element class designated as "Element 10" in FIG. 15 is exemplified by element descriptor P$DOF2.01, which has the consensus sequence WAAAGC (SEQ ID NO:26), see Yanagisawa S., et al. (1999) Plant J. 17:209-214. The P$AHPB element class is exemplified by the P$ATHB9.01 element descriptor, which has the consensus sequence GTAATGATTRC (SEQ ID NO:27), and is designated "Element 11" in FIG. 15, see Sessa G., et al. (1998) Plant Mol. Biol. 38:609-622.

Promoters of Promoter Configuration 1 are isolated nucleic acids having a plus strand and a minus strand and comprising, in combination and in 5' to 3' order, a P$MADS class element on the plus strand, a P$MYBS class element on the minus strand, and a P$DOFF class element on the plus strand, wherein the P$MADS class element is within about 50 nucleotides of the P$MYBS class element, the P$MYBS class element is within about 50 nucleotides of the P$DOFF class element, and the P$MADS class element is within about 100 nucleotides of the P$DOFF class element.

In another embodiment, the invention provides a plant promoter comprising a nucleic acid having a plus strand and a minus strand, the nucleic acid comprising, in combination and in 5' to 3' order, a P$MADS class element on the plus strand, a P$MYBS class element on the minus strand, and a P$DOFF class element on the plus strand, wherein the promoter is induced in roots of a plant by plant parasitic nematodes.

Promoters of Promoter Configuration 2 are isolated nucleic acids having a plus strand and a minus strand and comprising, in combination and in 5' to 3' order, a P$OPAQ class element on the plus strand, a first P$AHPB class element on the minus strand, a P$MADS class element on the plus strand, a second P$AHPB class element on the plus strand, and a P$TBPF class element on the plus strand, wherein the P$OPAQ class element is within about 60 nucleotides of the first P$AHPB class element, the first P$AHPB class element is within about 60 nucleotides of the P$MADS class element, the P$MADS class element is within about 60 nucleotides of the second P$AHPB class element, the second P$AHPB class element is within about 60 nucleotides of the P$TBPF class element and the P$OPAQ class element is within about 240 nucleotides of the P$TBPF class element.

In another embodiment, the invention provides a plant promoter comprising a nucleic acid having a plus strand and a minus strand, the nucleic acid comprising, in combination and in 5' to 3' order, a P$OPAQ class element on the plus strand, a first P$AHPB class element on the minus strand, a P$MADS class element on the plus strand, a second P$AHPB class element on the plus strand, and a P$TBPF class element on the plus strand, wherein the promoter is induced in roots of a plant by plant parasitic nematodes.

Promoters of Promoter Configuration 3 are isolated nucleic acids having a plus strand and a minus strand and comprising, in combination and in 5' to 3' order, a P$TBPF class element on the plus strand, a first P$AHPB class element on the plus strand, a P$MADS class element on the plus strand, a first P$DOFF class element on the plus strand, a second P$DOFF class element on the minus strand, and a second P$AHPB class element on the plus strand, wherein the P$TBPF class element is within about 60 nucleotides of the first P$AHPB class element, the first P$AHPB class element is within about 60 nucleotides of the P$MADS class element, the P$MADS class element is within about 60 nucleotides of the first P$DOFF class element, the first P$DOFF class element is within about 60 nucleotides of the second P$DOFF class element, the second P$DOFF class element is within about 60 nucleotides of the second P$AHPB class element and the P$TBPF class element is within about 300 nucleotides of the second P$AHPB class element.

In another embodiment, the invention provides a plant promoter comprising a nucleic acid having a plus strand and a minus strand, the nucleic acid comprising, in combination and in 5' to 3' order, a P$TBPF class element on the plus strand, a first P$AHPB class element on the plus strand, a P$MADS class element on the plus strand, a first P$DOFF class element on the plus strand, a second P$DOFF class element on the minus strand, and a second P$AHPB class element on the plus strand, wherein the promoter is induced in roots of a plant by plant parasitic nematodes.

In another embodiment, the invention provides a plant promoter comprising a nucleic acid having a plus strand and a minus strand, the nucleic acid comprising, in combination and in 5' to 3' order on the same strand, one or more P$MADS class elements and at least one P$TBPF class element, wherein the promoter is induced in roots of a plant by plant parasitic nematodes. In another embodiment, the invention provides a plant promoter comprising a nucleic acid having a plus strand and a minus strand, the nucleic acid comprising, in combination and in 5' to 3' order on the same strand, a P$MADS class element followed by a P$TBPF class element followed by a second P$MADS class element, wherein there may be other elements intervening and the promoter is induced in roots of a plant by plant parasitic nematodes. In yet another embodiment, the invention provides a plant promoter comprising a nucleic acid having a plus strand and a minus strand, the nucleic acid comprising, in combination and in 5' to 3' order on the same strand, a first P$MADS class element followed within about 100 nucleotides by a P$TBPF class element followed within about 200 nucleotides by a second P$MADS class element, the first P$MADS class element is within about 300 nucleotides of the second P$MADS class element, and wherein there may be other elements intervening and the promoter is induced in roots of a plant by plant parasitic nematodes.

In another embodiment, the invention provides a plant promoter comprising a nucleic acid having a plus strand and a minus strand, the nucleic acid comprising, in combination and in 5' to 3' order on the same strand, a first P$MADS class element having element descriptor P$MADSB.01, a P$TBPF class element having element descriptor p$TATA.01, and a second P$MADS class element having element descriptor P$AGL2.01, wherein there may be other elements intervening and the promoter is induced in roots of a plant by plant parasitic nematodes. In yet another embodiment, the invention provides a plant promoter comprising a nucleic acid having a plus strand and a minus strand, the nucleic acid comprising, in combination and in 5' to 3' order on the same strand, a first P$MADS class element having element descriptor P$MADSB.01, followed within about 100 nucleotides a P$TBPF class element having element descriptor p$TATA.01, and followed within about 200 nucleotides a second P$MADS class element having element descriptor P$AGL2.01, the first P$MADS class element within about 300 nucleotides of the second P$MADS class element, and wherein there may be other elements intervening and the promoter is induced in roots of a plant by plant parasitic nematodes.

The invention is also embodied in expression cassettes comprising the promoters of the invention. "Expression cassette" in this context is to be understood broadly as comprising all sequences contained in the cassette which may influence transcription of a nucleic acid of interest and, if applicable, translation thereof. In addition to the promoters of the invention, the expression cassette of the invention may further comprise regulatory elements that improve the function of the promoter, genetic elements that allow transcription and/or translation in prokaryotic and/or eukaryotic organisms, and downstream (in 3-direction) regulatory elements such as a transcription termination sequence and a polyadenylation sequence. The various components of the expression cassette of the invention are sequentially and operably linked together.

Accordingly, an expression cassette of the invention may comprise an isolated nucleic acid selected from the group consisting of a nucleic acid having a sequence as set forth in SEQ ID NO:1; a nucleic acid that hybridizes under stringent conditions to a nucleic acid having a sequence as set forth in SEQ ID NO:1; a nucleic acid comprising nucleotides 1554 to 1887 of a sequence as set forth in SEQ ID NO:1; a nucleic acid that hybridizes under stringent conditions to a nucleic acid comprising nucleotides 1554 to 1887 of a sequence as set forth in SEQ ID NO:1; a nucleic acid having a sequence as set forth in SEQ ID NO:2; a nucleic acid that hybridizes under stringent conditions to a nucleic acid having a sequence as set forth in SEQ ID NO:2; a nucleic acid comprising nucleotides 1569 to 1902 of a sequence as set forth in SEQ ID NO:2; a nucleic acid that hybridizes under stringent conditions to a nucleic acid comprising nucleotides 1569 to 1902 of a sequence as set forth in SEQ ID NO:2; a nucleic acid having a sequence as set forth in SEQ ID NO:3; a nucleic acid that hybridizes under stringent conditions to a nucleic acid having a sequence as set forth in SEQ ID NO:3; a nucleic acid comprising nucleotides 364 to 697 of a sequence as set forth in SEQ ID NO:3; a nucleic acid that hybridizes under stringent conditions to a nucleic acid comprising nucleotides 364 to 697 of a sequence as set forth in SEQ ID NO:3; a nucleic acid of Promoter Configuration 1; a nucleic acid of Promoter Configuration 2; and a nucleic acid of Promoter Configuration 3. Alternatively, an expression cassette of the invention comprises a promoter selected from the group consisting of (a) an isolated nucleic acid having a plus strand and a minus strand, the nucleic acid comprising, in combination and in 5' to 3' order, a P$MADS class element on the plus strand, a P$MYBS class element on the minus strand, and a P$DOFF class element on the plus strand; (b) an isolated nucleic acid having a plus strand and a minus strand, the nucleic acid comprising, in combination and in 5' to 3' order, a P$OPAQ class element on the plus strand, a first P$AHPB class element on the minus strand, a P$MADS class element on the plus strand, a second P$AHPB class element on the plus strand, and a P$TBPF class element on the plus strand; and (c) an isolated plant promoter having a plus strand and a minus strand, the promoter comprising, in combination and in 5' to 3' order, a P$TBPF class element on the plus strand, a first P$AHPB class element on the plus strand, a P$MADS class element on the plus strand, a first P$DOFF class element on the plus strand, a second P$DOFF class element on the minus strand, and a second P$AHPB class element on the plus strand; wherein the promoter is induced in roots of a plant by plant parasitic nematodes.

Alternatively, an expression cassette of the invention comprises a promoter comprising an isolated nucleic acid having a plus strand and a minus strand, the nucleic acid comprising, in combination and in 5' to 3' order on the same strand, one or more P$MADS class elements and at least one P$TBPF class element, wherein the promoter is induced in roots of a plant by plant parasitic nematodes. In another embodiment, an expression cassette of the invention comprises a promoter comprising an isolated nucleic acid having a plus strand and a minus strand, the nucleic acid comprising, in combination and in 5' to 3' order on the same strand, a P$MADS class element followed by a P$TBPF class element followed by a second P$MADS class element, wherein there may be other elements intervening and the promoter is induced in roots of a plant by plant parasitic nematodes. In yet another embodiment, an expression cassette of the invention comprises a promoter comprising an isolated nucleic acid having a plus strand and a minus strand, the nucleic acid comprising, in combination and in 5' to 3' order on the same strand, a first P$MADS class element followed within about 100 nucleotides by a P$TBPF class element followed within about 200 nucleotides by a second P$MADS class element, the first P$MADS class element within about 300 nucleotides of the second P$MADS class element, and wherein there may be other elements intervening and the promoter is induced in roots of a plant by plant parasitic nematodes.

In another embodiment, an expression cassette of the invention comprises a promoter comprising an isolated nucleic acid having a plus strand and a minus strand, the nucleic acid comprising, in combination and in 5' to 3' order on the same strand, a P$MADS class element having element descriptor P$MADSB.01, a P$TBPF class element having element descriptor p$TATA.01, and a P$MADS class element having element descriptor P$AGL2.01, wherein there may be other elements intervening and the promoter is induced in roots of a plant by plant parasitic nematodes. In yet another embodiment, an expression cassette of the invention comprises a promoter comprising an isolated nucleic acid comprising, in combination and in 5' to 3' order on the same strand, a P$MADS class element having element descriptor P$MADSB.01, followed within about 100 nucleotides a P$TBPF class element having element descriptor p$TATA.01, and followed within about 200 nucleotides a P$MADS class element having element descriptor P$AGL2.01, the first P$MADS class element within about 300 nucleotides of the second P$MADS class element, wherein there may be other elements intervening and the promoter is induced in roots of a plant by plant parasitic nematodes.

Specific genetic elements that may optionally be included in the expression cassette of the invention include, without limitation, origins of replication to allow replication in bacteria, e.g., the ORI region from pBR322 or the P15A ori; or elements required for *Agrobacterium* TDNA transfer, such as, for example, the left and/or rights border of the T-DNA. Other components of the expression cassette of the invention may include, without limitation, additional regulatory elements such as, for example, enhancers, introns, polylinkers, multiple cloning sites, operators, repressor binding sites, transcription factor binding sites, and the like. Exemplary enhancers include elements from the CaMV 35S promoter, octopine synthase genes (Ellis el al., 1987), the rice actin I gene, the maize alcohol dehydrogenase gene (Callis 1987), the maize shrunken I gene (Vasil 1989), TMV Omega element (Gallie 1989) and promoters from non-plant eukaryotes (e.g. yeast; Ma 1988). Exemplary plant intron sequences include introns from Adh1, bronze1, actin1, actin 2 (WO 00/760067), or the sucrose synthase intron; see: The Maize Handbook, Chapter 116, Freeling and Walbot, Eds., Springer, New York (1994).

Viral leader sequences may also enhance transcription of nucleic acids of interest by the expression cassette of the invention. For example, leader sequences from Tobacco Mosaic Virus (TMV), Maize Chlorotic Mottle Virus (MCMV), and Alfalfa Mosaic Virus (AMV) have been shown to be effective in enhancing expression. Other leaders known in the art include but are not limited to: Picornavirus leaders, for example, (Encephalomyocarditis virus (EMCV) leader; Potyvirus leaders, Tobacco Etch Virus (TEV) leader; MDMV leader (Maize Dwarf Mosaic Virus); Human immunoglobulin heavy-chain binding protein (BiP) leader, Untranslated leader from the coat protein mRNA of alfalfa mosaic virus (AMV RNA 4).

The expression cassette of the invention may also comprise a transcription termination element or polyadenylation signal. Exemplary transcription termination elements include those from the nopaline synthase gene of *Agrobacterium tumefaciens* (Bevan 1983), the terminator for the T7 transcript from the octopine synthase gene of *Agrobacterium tumefaciens*, and the 3' end of the protease inhibitor I or II genes from potato or tomato.

A second nucleic acid to be transcribed into RNA, and, optionally, expressed as a protein is inserted into the expression cassette of the invention for transformation into an organism. In accordance with the invention, the second nucleic acid sequence is placed downstream (i.e., in 3'-direction) of the promoter of the invention and upstream of the transcription termination elements, in covalent linkage therewith. Preferably, the distance between the second nucleic acid sequence and the promoter of the invention is not more than 200 base pairs, more preferably not more than 100 base pairs, most preferably no more than 50 base pairs.

An expression cassette of the invention may also be assembled by inserting a promoter of the invention into the plant genome. Such insertion will result in an operable linkage to a nucleic acid sequence of interest native to the genome. Such insertions allow the nucleic acid of interest to be expressed or over-expressed preferentially in root tissue, after induction by nematodes, as the result of the transcription regulating properties of the promoter of the invention. The insertion may be directed or by chance. Preferably the insertion is directed and realized by, for example, homologous recombination. By this procedure a natural promoter may be replaced by the promoter of the invention, thereby modifying the expression profile of an endogenous gene. The promoter may also be inserted in a way, that antisense mRNA of an endogenous gene is expressed, thereby inducing gene silencing.

The expression cassette of the invention may be inserted into a recombinant vector, plasmid, cosmid, YAC (yeast artificial chromosome), BAC (bacterial artificial chromosome), or any other vector suitable for transformation into host cell. Preferred host cells are bacterial cells and plant cells. When the host cell is a plant cell, the expression cassette or vector may become inserted into the genome of the transformed plant cell. Alternatively, the expression cassette or vector may be maintained extra chromosomally. The expression cassette or vector of the invention may be present in the nucleus, chloroplast, mitochondria, and/or plastid of the cells of the plant. Preferably, the expression cassette or vector of the invention is inserted into the chromosomal DNA of the plant cell nucleus.

The expression cassette of the invention may be transformed into a plant to provide a transgenic plant comprising a second nucleic acid in operative association with a plant promoter of the invention. The transgenic plant of this embodiment comprises a promoter comprising a nucleic acid sequence as set forth in SEQ ID NO:1, SEQ ID NO:2, SEQ ID NO:3, a minimal promoter fragment of SEQ ID NO:1, a minimal promoter fragment of SEQ ID NO:2, or a minimal promoter fragment of SEQ ID NO:3. Alternatively, the transgenic plant of the invention comprises a nucleic acid that hybridizes under stringent conditions to a promoter comprising a nucleic acid sequence as set forth in SEQ ID NO:1, SEQ ID NO:2, SEQ ID NO:3, a minimal promoter fragment of SEQ ID NO:1, a minimal promoter fragment of SEQ ID NO:2, or a minimal promoter fragment of SEQ ID NO:3, In another embodiment, the transgenic plant comprises a promoter of Promoter Configuration 1, Promoter Configuration 2, or Promoter Configuration 3.

The transgenic plants of the invention are made using transformation methods known to those of skill in the art of plant biotechnology. Any method may be used to transform the recombinant expression vector into plant cells to yield the transgenic plants of the invention. Suitable methods for transforming or transfecting host cells including plant cells can be found, for example, in Sambrook et al. supra, and in other laboratory manuals such as Methods in Molecular Biology, 1995, Vol. 44, *Agrobacterium* protocols, Ed: Gartland and Davey, Humana Press, Totowa, N.J.

General methods for transforming dicotyledenous plants are also disclosed, for example, in U.S. Pat. Nos. 4,940,838; 5,464,763, and the like. Methods for transforming specific dicotyledenous plants, for example, cotton, are set forth in U.S. Pat. Nos. 5,004,863; 5,159,135; and 5,846,797. Soybean transformation methods are set forth in U.S. Pat. Nos. 4,992, 375; 5,416,011; 5,569,834; 5,824,877; 6,384,301 and in EP 0301749B1. Other plant transformation methods are disclosed, for example, in U.S. Pat. Nos. 4,945,050; 5,188,958; 5,596,131; 5,981,840, and the like.

The transgenic plants of the invention may be crossed with similar transgenic plants or with plants lacking the promoter of the invention and second nucleic acid, using known methods of plant breeding, to prepare seed. The seed is then planted to obtain a crossed fertile transgenic plant comprising the nucleic acid of interest and the promoter of the invention. The plant may be a monocot or a dicot. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants.

The invention is further embodied in a crop comprising a plurality of the transgenic plants of the invention, planted together in an agricultural field.

The transgenic plants of the invention may be used in a method of controlling infestation of a crop by a plant parasitic nematode, which comprises the step of growing said crop from seeds comprising an expression cassette comprising a plant promoter of the invention in operative association with a second nucleic acid that encodes an agent that disrupts the growth, development and/or reproduction of said plant parasitic nematode, wherein the expression cassette is stably integrated into the genomes of the seeds. Such nematode-toxic disrupting agents include, without limitation, a double stranded RNA which is substantially identical to a target gene of a parasitic plant nematode which is essential for survival, metamorphosis, or reproduction of the nematode; a double stranded RNA which is substantially identical to a plant gene required to maintain a nematode feeding site; a microbial toxin; a toxin derived from an insect, and the like.

The following examples are not intended to limit the scope of the claims to the invention, but are rather intended to be exemplary of certain embodiments. Any variations in the exemplified methods that occur to the skilled artisan are intended to fall within the scope of the present invention.

Example 1

Cloning of Plant Drug/Metabolite Exporter Gene Promoters from *Arabidopsis*

*Arabidopsis* (Columbia ecotype) genomic DNA was extracted using the Qiagen DNAeasy Plant Minikit (Qiagen). The 1,967 bp (SEQ ID NO:1) and 1,950 bp (SEQ ID NO:2) genomic DNA regions (putative promoter sequences) directly upstream of the ATG codon including 5'-untranslated region corresponding to *Arabidopsis* plant metabolite exporter genes with locus identifiers, At1g21890 and At4g08290 respectively, were cloned using standard PCR amplification protocol. For this, approximately 0.1 μg of *Arabidopsis* genomic DNA was used as the DNA template in the PCR reaction. The primers used for PCR amplification of the *Arabidopsis* promoter sequences are shown in FIG. 11 and were designed based on the *Arabidopsis* Genomic sequence Database (TAIR). The primer sequences described by SEQ ID NO:7 and SEQ ID NO:9 contain the PstI restriction site for ease of cloning. The primer sequences described by SEQ ID NO:8 and SEQ ID NO:10 contain the AscI site for ease of cloning. Primer sequences described by SEQ ID NO:7 and SEQ ID NO:8 were used to amplify the promoter region of *Arabidopsis* locus At1g21890. Primer sequences described by SEQ ID NO:9 and SEQ ID NO:10 were used to amplify the promoter region of *Arabidopsis* locus At4g08290.

The amplification reaction mix contained the following: 2.5 μl 10× Hot Start Buffer; 0.15 μl Hot Start Taq DNA polymerase; 0.5 μl 10 mM dNTPs; 0.5 μl 10 μM primer A; 0.5 μl 10 uM primer B; 1.0 μl *Arabidopsis* genomic DNA (approximately 100 ng); 19.85 μl water. Thermocycler: T3 Thermocycler Biometra, Germany was used for the amplification using the following setting: 1 cycle with 900 seconds at 94° C.; 5 cycles with 30 seconds at 94° C., 30 seconds at 52° C., and 120 seconds at 72° C.; 30 cycles with 30 seconds at 94° C., 30 seconds at 62° C., and 120 seconds at 72° C.; 1 cycle with 300 seconds at 72° C.

The amplified DNA fragment size for each PCR product was verified by standard agarose gel electrophoresis and the DNA extracted from gel by Qiagen Gel Extraction Kit (Qiagen, Hilden, Germany). The purified fragments were TOPO cloned into pCR2.1 using the TOPO TA cloning kit following the manufacturer's instructions (Invitrogen). The cloned fragments were sequenced using an Applied Biosystem 373A (ABI) automated sequencer and verified to be the expected sequence by using the sequence alignment clustalW from the sequence analysis tool Vector NTI. The 1,967 bp and 1,950 bp DNA fragments corresponding to the promoter regions of At1g21890 and At4g08290 are shown as SEQ ID NO:1 and SEQ ID NO:2. The restriction sites introduced in the primers for facilitating cloning are not included in the sequences.

Example 2

Cloning of MtN21-Like Metabolite Exporter Gene Promoters from Soybean

As described more fully in commonly assigned US patent application, U.S. Ser. No. 60/743,340, incorporated herein by reference in its entirety, two polynucleotides encoding soybean MtN21 homologs, GmMtN21-1 (GM50862200, SEQ ID NO:5) and GmMtN21-2 (GM50444087, SEQ ID NO:4) were identified as being up-regulated in syncytia of SCN-infected soybean roots, using a bioinformatics approach. FIG. 4 depicts the sequences of GmMtN21-1 and GmMtN21-2. The GmMtN21-2 cDNA sequence (SEQ ID NO:4) was determined to be full-length since there is a TAG stop codon starting at bp 59 upstream and in the same frame as the ATG start codon of the encoded Mtn21 open reading frame which starts at base pair 74. The alignment of the sequences of GmMtN21-2 (designated GM50444087, SEQ ID NO:4) and GmMtN21-1 (designated GM50862200, SEQ ID NO:5) shown in FIG. 12 indicates that GmMtN21-1 is likely to be a partial sequence missing approximately 200 amino acids at the N-terminal end.

To clone the promoter sequence of GmMtN21, the Universal Genome Walking Kit (Clontech Laboratories Inc., Palo Alto, Calif.) was used according to the manufacturer's instructions. For this, soybean (*Glycine max*, Resnik) genomic DNA was extracted using the Qiagen DNAeasy Plant Minikit (Qiagen). The procedure consisted of two PCR amplifications, using an adapter primer and a gene-specific primer for each amplification reaction. The sequences of primers used to isolate the promoters of the invention are shown in FIG. 11. The gene specific primers which target GmMtN21-2 (SEQ ID NO:4) were primary primer, GmMtN21-2 GW (SEQ ID NO:11) and nested primer, GmMtN21-2GWnest (SEQ ID NO:12). The adaptor primers used were GmMtN21-2GW AP1 (SEQ ID NO:13) and GmMtN21-2GW AP2 (SEQ ID NO:14). Using this protocol, several clones were isolated and sequenced.

The longest cloned product was identified as pAW121 (SEQ ID NO:6). A sequence alignment of pAW121 with GmMtN21-2 indicated that this clone is highly homologous but not identical to GmMtN21-2 (SEQ ID NO:4) as shown in FIG. 5. Therefore, pAW121 sequence was likely to be derived from a homolog of GmMtN21-2 and was named GmMtN21-3. The alignment also revealed that pAW121 contained a 122 base-pair intron in the coding region from nucleotide 1101 to 1223 and a 791 bp promoter sequence upstream of the ATG from nucleotide 126 to 916 (see FIG. 13). This promoter region was cloned out of pAW121 using standard PCR techniques and the primers GmMtN21-3 promFor (SEQ ID NO:15) and GmMtN21-3 promRev (SEQ ID NO:16). GmMtN21-3promFor and GmMtN21-3promRev carried the enzyme restriction sites for PstI and AscI respectively for ease of directional cloning. The GmMtN21-3 promoter and the 5'UTR sequences, without the restriction sites used for cloning, is shown as SEQ ID NO:3. Nucleotide sequence 1-697 represents the entire promoter sequence with the core promoter region spanning nucleotides 364-697. The TATA signal spans nucleotide 664-670 and the 5' untranslated leader sequence of the mRNA from nucleotides 697-791.

Example 3

Figure 7:
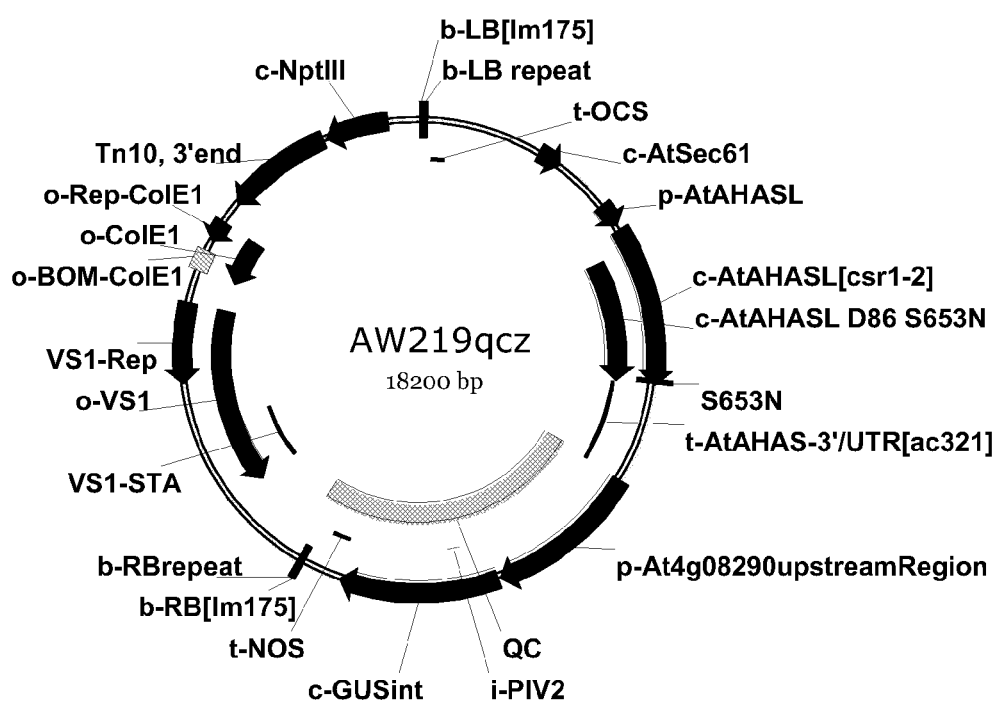
FIG. 7: Map of binary vector pAW219qcz containing the *A. thaliana* promoter of locus At4g08290 (SEQ ID NO:2)
Figure 8:
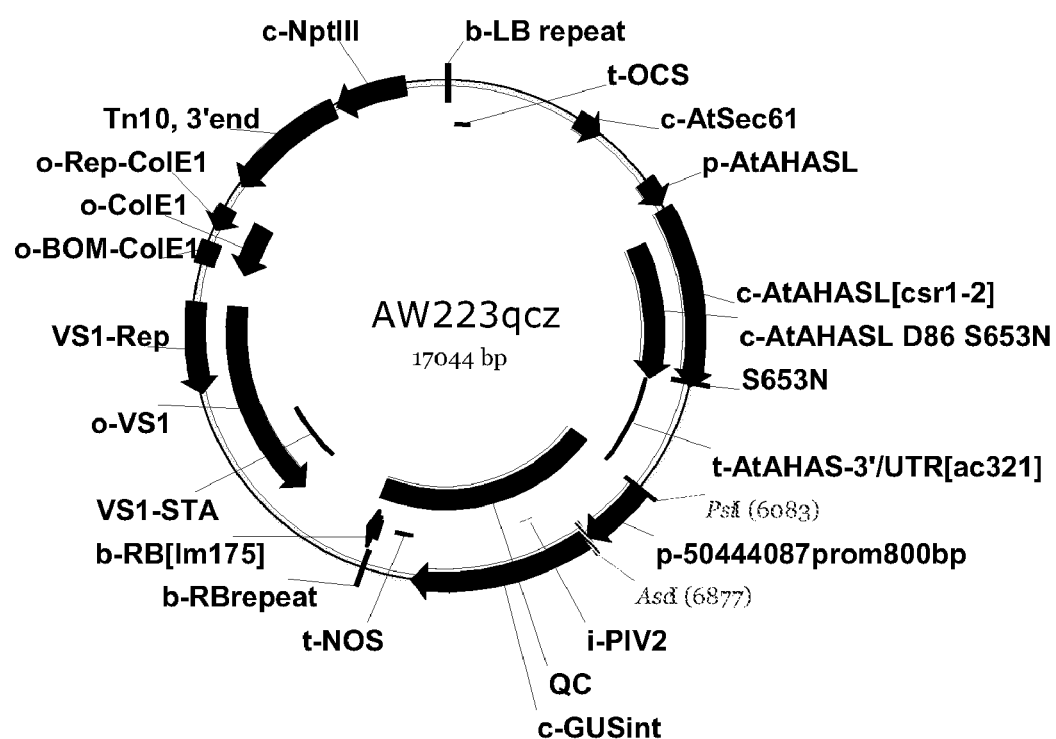
FIG. 8: Map of binary vector pAW223qcz containing the GmMtN21-3 promoter (SEQ ID NO:3).

Binary Vector Construction for Transformation and Generation of Transgenic Hairy Roots To evaluate the expression activity of the cloned promoters, gene fragments corresponding to nucleotides 1-1967 of SEQ ID NO:1, nucleotides 1-1947 of SEQ ID NO:2 and nucleotides 1-791 of SEQ ID NO:3 were cloned upstream of a GUS reporter gene (bacterial β-glucuronidase or GUS gene (Jefferson (1987) EMBO J. 6, 3901-3907) to create the binary vectors pAW134qcz, pAW219qcz, and pAW223qcz, respectively, as shown in FIGS. 6 through 8. The plant selection marker in the binary vectors was a mutated AHAS gene from *A. thaliana* that conferred tolerance to the herbicide ARSENAL (imazapyr, BASF Corporation, Florham Park, N.J.). The selectable marker mutated AHAS was driven by the *Arabidopsis* AHAS promoter.

The soybean cyst nematode can be propagated on normal soybean root explants. However, this technique requires the continual establishment of root explants because these organs have a determinant period of growth in culture. In contrast, soybean hairy roots generated by infecting soybean cotyledons with *A. rhizogenes* exhibit indeterminate growth in tissue culture providing an alternative to normal root explants for monoxenic propagation and study of soybean cyst nematode (Cho et. al., (1998) Plant Sci. 138, 53-65). The *A. rhizogenes* can transfer the T-DNA of binary vectors in trans, thereby enabling the production of transgenic hairy roots containing foreign genes inserted in the T-DNA plasmid. This method has been used to produce transgenic roots in several plant species (Christey, (1997) Doran, P. M. (ed) Hairy roots: culture and application, Harwood, Amsterdam, pp. 99-111). The transgenic hairy roots can then be used to study the effect of transgene expression on any given phenotype.

In the present example, binary vectors pAW134qcz, pAW219qcz, and pAW223qcz were transformed into *A. rhizogenes* K599 strain by electroporation (Cho et al., supra). The transformed *Agrobacterium* was used to induce soybean hairy-root formation using the following protocol. Approximately five days before *A. rhizogenes* inoculation, seeds from soybean cultivar Williams 82 (SCN-susceptible) were sterilized with 10% bleach for 10 minutes and germinated on 1% agar at 25° C. with 16-hour/day lighting. Approximately three days before *A. rhizogenes* inoculation, a frozen stock of *A. rhizogenes* Strain K599 containing the binary vector was streaked on LB+kanamycin (50 µg/ml) plates and incubated at 28° C. in darkness. Approximately one day before *A. rhizogenes* inoculation, a colony was picked from the plate and inoculated into liquid LB+kanamycin (50 µg/ml). The culture was shaken at 28° C. for approximately 16 hours. The concentration of *A. rhizogenes* in the liquid culture was adjusted to $OD_{600}=1.0$.

Cotyledons were excised from soybean seedlings and the adaxial side was wounded several times with a scalpel. 15 µl of *A. rhizogenes* suspension was inoculated onto the wounded surface, and the cotyledon was placed with the adaxial side up on a 1% agar plate for 3 days at 25° C. under 16 hour/day lighting. The cotyledons were then transferred onto MS plates containing 500 µg/ml Carbenicillin (to suppress *A. rhizogenes*) and 1 µM ARSENAL. After culturing the cotyledons on selection media for 2 weeks, hairy roots were induced from the wounding site. The roots resistant to ARSENAL and growing on the selection media were harvested and transferred onto fresh selection media of the same composition and incubated at 25° C. in darkness. Two weeks after harvesting hairy roots and culturing them on selection media, the hairy roots were subcultured onto MS media containing Carbenicillin 500 µg/ml but not ARSENAL.

Example 4

Detection of Promoter Activity in Soybean Hairy Roots

As set forth in Example 3, the promoters of the invention were placed in operative association with the GUS reporter gene to determine their expression activity. The β-glucuronidase activity of the GUS gene can be detected in planta by means of a chromogenic substance such as 5-bromo-4-chloro-3-indoyl-β-D-glucuronic acid (x-Gluc) in an activity staining reaction (Jefferson, supra).

To study the promoter activity of SEQ ID NOs: 1-3 in the presence and absence of nematode infection, several independent transgenic lines were generated from transformation with pAW134qcz, pAW219qcz, and pAW223qcz. Approximately three weeks after subculturing, the transgenic hairy-root lines on MS, were inoculated with surface-decontaminated J2 of SCN race 3 at the 2000 J2/plate level. At 7 and 12 days after inoculation (DAI), the roots were harvested by removing from the agar plates and gently rinsed with changes in water and stained in GUS staining solution containing X-Gluc (2 mg/l) at 37° C. for 16 hours. At each time point after inoculation, a non-inoculated control plate from each line was also stained in GUS staining solution. After GUS staining, the roots were stained in acid fuchsin and then destained to visualize the nematodes, which were stained red. The roots were then observed under a microscope for detection of GUS expression.

For each transgenic line, 10 randomly picked syncytia were observed and scored for intensity of GUS expression at 7 and 12 days after infection (DAI). The following scoring index was used: "−" for no GUS staining, "+" for weak GUS staining, and "++" for strong GUS staining. A round-up average of the 10 counts was used to determine the GUS expression level in the syncytia for that line. In addition, GUS expression level in the same lines for other root tissues such as callus, root-tip, vasculature, cortical and primordial were also recorded using the same GUS scoring index of "−", "+" and "++". The results for lines transformed with pAW134qcz, pAW219qcz, and pAW223qcz are presented in FIG. 9.

In order to more accurately define the promoter region of At1g21890 (SEQ ID NO:1), shorter fragments of the upstream sequence were tested. Both the approximately 1000 bp and 500 bp sequences were able to confer nematode-induced expression in syncytia, indicating that all of the required regulatory elements are found within the region 500 bp upstream of the start codon. These results are consistent with the results of the promoter analyses using Genomatix set forth in Example 6.

The result of the GUS staining indicates that for most lines tested, the promoter fragment in pAW134 showed intermediate to strong GUS expression in the syncytia at 7 DAI and 12 DAI. In contrast, GUS expression in other root parts such as root tips and root cortex was undetected or very weak. There was, however, some expression of the promoter in the vascular tissue in both nematode inoculated and control non-inoculated samples.

Example 5

PLACE Analysis of Promoters

PLACE analysis results indicate a TATA box localized at base pair 1854 to base pair 1860 of SEQ ID NO:1 as shown in FIG. 1. In consequence, the 5' untranslated region starts at about base pair 1887. The TAIR website also predicts the start of the 5' untranslated region at base pair 1887. The sequence described by SEQ ID NO:1 ends 0 base pairs before the ATG start codon. The potential core region of the promoter described by SEQ ID NO:1 is from bases 1554 to 1887.

PLACE analysis results indicate a TATA box localized at base pair 1869 to base pair 1875 of SEQ ID NO:2 as shown in FIG. 2. In consequence, the 5' untranslated region starts at about base pair 1902. The TAIR website predicts the start of the 5' untranslated region at base pair 1766. The sequence described by SEQ ID NO:2 ends 0 base pairs before the ATG start codon. The potential core region of the promoter described by SEQ ID NO:2 is from bases 1569 to 1902.

PLACE results indicate a TATA box localized at base pair 664 to base pair 670 of SEQ ID NO:3 as shown in FIG. 3. In consequence, the 5' untranslated region starts at about base pair 697. The potential core region of the promoter described by SEQ ID NO:3 is from bases 364-697.

Example 6

Identification of Promoter Configuration 1, Promoter Configuration 2, and Promoter Configuration 3

Genomatix is a promoter sequence analysis software application containing DiAlign and FrameWorker (Genomatrix, Munich, Germany) algorithms. DiAlign is a multiple-sequence alignment tool and FrameWorker can scan a set of DNA sequences for orientation and distance correlated transcription factor binding sites (promoter element classes).

The 3'650 bp of SEQ ID NO:1, SEQ ID NO:2, and SEQ ID NO:3 were used for the two Genomatix analyses described above. This corresponds to bases 1318 to 1967 of SEQ ID NO:1, bases 1298 to 1947 of SEQ ID NO:2, and bases 142 to 791 of SEQ ID NO:3.

To determine if there was sequence homology between bases 1318 to 1967 of SEQ ID NO:1, bases 1298 to 1947 of SEQ ID NO:2, and bases 142 to 791 of SEQ ID NO:3 the Genomatix DiAlign program was used. The result of this analysis is shown in FIG. 14. This analysis shows that bases 1318 to 1967 of SEQ ID NO:1 is most similar to bases 142 to 791 of SEQ ID NO:3 (24% sequence identity). Because of this, bases 1318 to 1967 of SEQ ID NO:1 were compared to bases 142 to 791 of SEQ ID NO:3 using the Genomatix FrameWorker algorithm to determine a common configuration of plant promoter element classes using the default parameters. Multiple Promoter Configuration models were identified in this analysis.

An additional analysis was done expanding the distance between promoter elements from 50 bp (default) to 60 bp. This second analysis also produced multiple Promoter Configuration models. Promoter Configuration 1, Promoter Configuration 2, and Promoter Configuration 3 were generated which comprise 3, 5, and 6 promoter elements, respectively, as summarized in FIG. 10. The model containing three promoter element classes was designated Promoter Configuration 1. The model containing five promoter element classes was designated Promoter Configuration 2. The model containing six promoter element classes was designated Promoter Configuration 3. The locations of promoter element classes contained in the promoter sequences of SEQ ID NO:1 and SEQ ID NO:3 are shown in FIG. 1 and FIG. 3, respectively. In addition, FIG. 15 shows the common spatial orientation of the promoter element classes in all three Promoter Configurations.

Example 7

Cloning deletions of At1g21890 (SEQ ID NO:1) Promoter

Figure 16:
FIG. 16: Feeding site β-glucuronidase expression patterns of binary vectors pAW134qcz, RTJ137, RTJ141, RTJ142, pAW329, RTJ133, RTJ134, RTJ135, and RTJ136 (See Examples 7 and 8) in the soybean hairy root assay set forth in Example 9. The following scoring index was used: "−" for no staining, "+" for weak staining, "++" for strong staining. Also, "+/−" indicates that 1 line out of 12 showed GUS staining in the feeding site in less than or equal to 7 out of 10 observed feeding sites. Because only 1 line showed activity in the feeding site, the score is not consistent with a true positive expression pattern and may be the result of a positional effect.

In order to further define the promoter region of At1g21890 (SEQ ID NO:1), a total of eight constructs containing promoter deletion fragments of A. thaliana locus At1g21890 promoter (SEQ ID NO:1) were generated. All promoter deletion constructs are contained in the same vector backbone as pAW134qcz shown in FIG. 6. Results from these constructs were used to determine if elements described in Promoter Configuration 1, Promoter Configuration 2, and Promoter Configuration 3 (See FIG. 15) are necessary to drive expression in the SCN feeding site. An overview of promoter deletion constructs is described in FIG. 16. A 650 bp promoter fragment containing bases 1318 to 1967 of A. thaliana locus At1g21890 promoter (SEQ ID NO:1) containing promoter elements 1 through 11 described in FIG. 15 was generated and is represented by construct RTJ137. This promoter region was used to generate the Promoter Configurations described in FIG. 15 using the Genomatix software. A 635 bp promoter fragment including bases 1318 to 1637 and bases 1653 to 1967 containing promoter elements 1, 2, 3, 4, 5, 6, 7, 9, 10, and 11 of A. thaliana locus At1g21890 promoter (SEQ ID NO:1) was generated and is represented by construct RTJ141. A 629 bp promoter fragment including bases 1318 to 1713 and bases 1735 to 1967 containing promoter elements 2, 3, 4, 5, 6, 7, 8, 9, 10, and 11 of A. thaliana locus At1g21890 promoter (SEQ ID NO:1) was generated and is represented by construct RTJ142. A 442 bp promoter fragment including bases 1526 to 1967 of A. thaliana locus At1g21890 promoter (SEQ ID NO:1) and containing promoter elements 1, 2, 3, 5, 6, 7, 8, 9, 10, and 11 described in FIG. 15 was generated and is represented by construct pAW329. A 412 bp promoter fragment including bases 1556 to 1967 of A. thaliana locus At1g21890 promoter (SEQ ID NO:1) and containing promoter elements 1, 2, 3, 6, 7, 8, 9, 10, and 11 is represented by construct RTJ133. A 365 bp promoter fragment including bases 1603 to 1967 of A. thaliana locus At1g21890 promoter (SEQ ID NO:1) and containing promoter elements 1, 2, 3, 8, 9, 10, and 11 is represented by construct RTJ134. A 315 bp promoter fragment including bases 1653 to 1967 of A. thaliana locus At1g21890 promoter (SEQ ID NO:1) and containing promoter elements 1, 2, 3, 9, 10, and 11 is represented by construct RTJ135. A 258 bp promoter fragment including bases 1710 to 1967 of A. thaliana locus At1g21890 promoter (SEQ ID NO:1) and containing promoter elements 1, 2, 3, 10, and 11 is represented by construct RTJ136. In summary, Two promoter deletion fragments contained in constructs RTJ141 and RTJ142 were derived by removing a single element in each of the constructs to determine if either element is necessary for promoter activity in the SCN feeding site. Six promoter deletion constructs (RTJ137, pAW329, RTJ133, RTJ134, RTJ135, and RTJ136) were derived by generating 5' truncations of *A. thaliana* locus At1g21890 promoter (SEQ ID NO:1) as described.

DNA synthesis was utilized to generate the two promoter deletion fragments contained in RTJ141 and RTJ142. The promoter deletion fragments are identical to RTJ137 except that they are missing a single promoter element as described above. PstI and AscI were introduced into the synthesis fragments for the ease of cloning.

To generate the six 5' truncations of *A. thaliana* locus At1g21890 promoter (SEQ ID NO:1) plasmid DNA of pAW134qcz was extracted from *E. coli* using the Qiagen Plasmid miniprep kit (Qiagen). Promoter deletion fragments of *A. thaliana* locus At1g21890 promoter (SEQ ID NO:1) contained in pAW134qcz were amplified using standard PCR amplification protocol. For this, approximately 0.1 ug of pAW134qcz plasmid DNA (described in FIG. 6) was used as the DNA template in the PCR reaction. The primers used for PCR amplification of the *Arabidopsis* promoter sequences are shown in FIG. 11 and were designed based on the promoter sequence of *A. thaliana* locus At1g21890 promoter (SEQ ID NO:1) contained in pAW134qcz. The primer sequences described by SEQ ID NO:28, SEQ ID NO:29, SEQ ID NO:30, SEQ ID NO:31, SEQ ID NO:32, and SEQ ID NO:33 contain the PstI restriction site for ease of cloning. The primer sequence described by SEQ ID NO:34 anneals downstream of the AscI site in pAW134qcz such that the AscI site will be contained in the amplified fragment for ease of cloning. Primer sequences described by SEQ ID NO:28 and SEQ ID NO:34 were used to amplify the 650 bp promoter deletion region of *Arabidopsis* locus At1g21890 promoter contained in pAW134qcz used to generate RTJ137. Primer sequences described by SEQ ID NO:29 and SEQ ID NO:34 were used to amplify the 442 bp promoter deletion region of *Arabidopsis* locus At1g21890 promoter contained in pAW134qcz used to generate pAW329. Primer sequences described by SEQ ID NO:30 and SEQ ID NO:34 were used to amplify the 412 bp promoter deletion region of *Arabidopsis* locus At1g21890 promoter contained in pAW134qcz used to generate RTJ133. Primer sequences described by SEQ ID NO:31 and SEQ ID NO:34 were used to amplify the 365 bp promoter deletion region of *Arabidopsis* locus At1g21890 promoter contained in pAW134qcz used to generate RTJ134. Primer sequences described by SEQ ID NO:32 and SEQ ID NO:34 were used to amplify the 315 bp promoter deletion region of *Arabidopsis* locus At1g21890 promoter contained in pAW134qcz used to generate RTJ135. Primer sequences described by SEQ ID NO:33 and SEQ ID NO:34 were used to amplify the 258 bp promoter deletion region of *Arabidopsis* locus At1g21890 promoter contained in pAW134qcz used to generate RTJ136.

Amplification reaction mix contained the following: 2.5 µl 10×Pfu Turbo buffer; 0.5 µl Pfu Turbo DNA polymerase; 0.5 µl 10 mM dNTPs; 0.5 µl 10 µM primer A; 0.5 µl 10 µM primer B; 1.0 µl pAW134qcz plasmid DNA (approximately 100 ng); 19.50 µl water. Thermocycler: T3 Thermocycler Biometra, Germany was used for the amplification using the following setting: 1 cycle with 60 seconds at 94° C.; 32 cycles with 30 seconds at 94° C., 30 seconds at 52° C., and 120 seconds at 72° C.; 1 cycle with 300 sec at 72° C.

The amplified DNA fragment size for each PCR product was verified by standard agarose gel electrophoresis and the DNA extracted from gel by Qiagen Gel Extraction Kit (Qiagen, Hilden, Germany). The purified fragments were digested with PstI and AscI following the manufacturer's instructions (New England Biolabs). The digested fragments were purified using the Qiagen PCR purification kit (Qiagen). The 650 bp promoter deletion region of At1g21890 promoter amplified using primers SEQ ID NO:28 and SEQ ID NO:34 is represented by bases 1318 to 1967 of SEQ ID NO:1. The 442 bp promoter deletion region of At1g21890 promoter amplified using primers SEQ ID NO:29 and SEQ ID NO:34 is represented by bases 1526 to 1967 of SEQ ID NO:1. The 412 bp promoter deletion region of At1g21890 promoter amplified using primers SEQ ID NO:30 and SEQ ID NO:34 is represented by bases 1556 to 1967 of SEQ ID NO:1. The 365 bp promoter deletion region of At1g21890 promoter amplified using primers SEQ ID NO:31 and SEQ ID NO:34 is represented by bases 1603 to 1967 of SEQ ID NO:1. The 315 bp promoter deletion region of At1g21890 promoter amplified using primers SEQ ID NO:32 and SEQ ID NO:34 is represented by bases 1653 to 1967 of SEQ ID NO:1. The 258 bp promoter deletion region of At1g21890 promoter amplified using primers SEQ ID NO:33 and SEQ ID NO:34 is represented by bases 1710 to 1967 of SEQ ID NO:1. The restriction sites introduced in the primers for facilitating cloning are not included in the designated sequences.

Example 8

Binary Vector Construction At1g21890 Promoter Deletions for Transformation and Generation of Transgenic Hairy Roots To evaluate the expression activity of the cloned promoter deletions derived from pAW134qcz, gene fragments corresponding to nucleotides 1318 to 1967, 1526 to 1967, 1556 to 1967, 1603 to 1967, 1653 to 1967, and 1710 to 1967 of SEQ ID NO:1 were cloned upstream of a GUS reporter gene (bacterial β-glucuronidase or GUS gene (Jefferson (1987) EMBO J. 6, 3901-3907) to create the binary vectors RTJ137, pAW329, RTJ133, RTJ134, RTJ135, RTJ136, respectively. To evaluate the expression activity of the cloned promoter deletions derived from pAW134qcz, the synthesized gene fragment corresponding to nucleotides 1318 to 1637 and bases 1653 to 1967 of SEQ ID NO:1 were cloned upstream of a GUS reporter gene (bacterial β-glucuronidase or GUS gene (Jefferson (1987) EMBO J. 6, 3901-3907) to create the binary vector RTJ141. To evaluate the expression activity of the cloned promoter deletions derived from pAW134qcz, the synthesized gene fragment corresponding to nucleotides 1318 to 1713 and bases 1735 to 1967 of SEQ ID NO:1 were cloned upstream of a GUS reporter gene (bacterial β-glucuronidase or GUS gene (Jefferson (1987) EMBO J. 6, 3901-3907) to create the binary vector RTJ142. The plant selection marker in the binary vectors was a mutated AHAS gene from *A. thaliana* that conferred tolerance to the herbicide ARSENAL (imazapyr, BASF Corporation, Florham Park, N.J.). The selectable marker mutated AHAS was driven by the *Arabidopsis* AHAS promoter.

The soybean cyst nematode can be propagated on normal soybean root explants. However, this technique requires the continual establishment of root explants because these organs have a determinant period of growth in culture. In contrast, soybean hairy roots generated by infecting soybean cotyledons with *A. rhizogenes* exhibit indeterminate growth in tissue culture providing an alternative to normal root explants for monoxenic propagation and study of soybean cyst nematode (Cho et. al., (1998) Plant Sci. 138, 53-65). The *A. rhizogenes* can transfer the T-DNA of binary vectors in trans, thereby enabling the production of transgenic hairy roots containing foreign genes inserted in the T-DNA plasmid. This method has been used to produce transgenic roots in several plant species (Christey, (1997) Doran, P. M. (ed) Hairy roots: culture and application, Harwood, Amsterdam, pp. 99-111). The transgenic hairy roots can then be used to study the effect of transgene expression on any given phenotype.

In the present example, binary vectors RTJ137, pAW329, RTJ133, RTJ134, RTJ135, RTJ136, RTJ141, and RTJ142 were transformed into *A. rhizogenes* K599 strain by electroporation (Cho et al., supra). The transformed *Agrobacterium* was used to induce soybean hairy-root formation using the following protocol. Approximately five days before *A. rhizogenes* inoculation, seeds from soybean cultivar Williams 82 (SCN-susceptible) were sterilized with 10% bleach for 10 minutes and germinated on 1% agar at 25° C. with 16-hour/day lighting. Approximately three days before *A. rhizogenes* inoculation, a frozen stock of *A. rhizogenes* Strain K599 containing the binary vector was streaked on LB+kanamycin (50 µg/ml) plates and incubated at 28° C. in darkness. Approximately one day before *A. rhizogenes* inoculation, a colony was picked from the plate and inoculated into liquid LB+kanamycin (50 µg/ml). The culture was shaken at 28° C. for approximately 16 hours. The concentration of *A. rhizogenes* in the liquid culture was adjusted to $OD_{600}=1.0$.

Cotyledons were excised from soybean seedlings and the adaxial side was wounded several times with a scalpel. 15 µl of *A. rhizogenes* suspension was inoculated onto the wounded surface, and the cotyledon was placed with the adaxial side up on a 1% agar plate for 3 days at 25° C. under 16 hour/day lighting. The cotyledons were then transferred onto MS plates containing 500 µg/ml Carbenicillin (to suppress *A. rhizogenes*) and 1 µM ARSENAL. After culturing the cotyledons on selection media for 2 weeks, hairy roots were induced from the wounding site. The roots resistant to ARSENAL and growing on the selection media were harvested and transferred onto fresh selection media of the same composition and incubated at 25° C. in darkness. Two weeks after harvesting hairy roots and culturing them on selection media, the hairy roots were subcultured onto MS media containing Carbenicillin 500 µg/ml but not ARSENAL.

Example 9

Detection of Promoter Deletion Activity in Soybean Hairy Roots

As set forth in Example 8, the promoters of the invention were placed in operative association with the GUS reporter gene to determine their expression activity. The β-glucuronidase activity of the GUS gene can be detected in planta by means of a chromogenic substance such as 5-bromo-4-chloro-3-indoyl-β-D-glucuronic acid (x-Gluc) in an activity staining reaction (Jefferson, supra).

To study the promoter activity of deletion of SEQ ID NO:1 in the presence and absence of nematode infection, several independent transgenic lines were generated from transformation with pAW134qcz, RTJ137, pAW329, RTJ133, RTJ134, RTJ135, RTJ136, RTJ141, and RTJ142. Approximately three weeks after subculturing, the transgenic hairy-root lines on MS, were inoculated with surface-decontaminated J2 of SCN race 3 at the 2000 J2/plate level. At 12 days after inoculation (DAI), the roots were harvested by removing from the agar plates and gently rinsed with changes in water and stained in GUS staining solution containing X-Gluc (2 mg/l) at 37° C. for 16 hours. At each time point after inoculation, a non-inoculated control plate from each line was also stained in GUS staining solution. The roots were then observed under a microscope for detection of GUS expression.

For each transgenic line, 10 randomly picked syncytia were observed and scored for intensity of GUS expression at 12 Days after infection (DAI). The following scoring index was used: "−" for no staining, "+" for weak staining, "++" for strong staining. The following scoring index was used: "−" for no staining, "+" for weak staining, "++" for strong staining. Also, "+/−." indicates that 1 line out of 12 showed GUS staining in the feeding site in lass less than or equal to 7 out of 10 observed feeding sites. Because only 1 line showed activity in the feeding site, the score is not consistent with a true positive expression pattern and may be the result of a positional effect. A round-up average of the 10 counts was used to determine the GUS expression level in the syncytia for each line.

In addition, GUS expression level in the same lines for other root tissues such as callus, root-tip, vasculature, cortical and primordial were also conducted for lines transformed with pAW134qcz, RTJ137, pAW329, RTJ133, RTJ134, RTJ135, RTJ136, RTJ141, and RTJ142. In all promoter deletion constructs expression in root tip, vascular, and cortical tissues were consistent with the "full-length" promoter contained in pAW134qcz and represented by SEQ ID NO:1.

In regard to syncytia expression, the 650, 442, and 412 bp promoter sequences contained in RTJ137, pAW329, and RTJ133, respectively, were able to confer nematode-induced expression in syncytia comparable to the 1967 bp promoter contained in pAW134qcz. This indicates that all the required regulatory elements are found within the 412 bp promoter contained in RTJ133 including promoter elements 1, 2, 3, 6, 7, 8, 9, 10, and 11 as described in FIG. 16. In particular, the 635 and 639 bp promoter sequences contained in RTJ141 and RTJ142, respectively, were not able to confer nematode-induced expression in syncytia, indicating that promoter element 8 and promoter element 1 are necessary for SCN-induced expression in the feeding site. In addition, the 365, 315, and 258 bp promoter sequences contained in RTJ134, RTJ135, and RTJ136, respectively, showed either no feeding site expression (RTJ134) or very reduced feeding site expression (RTJ135 and RTJ136) compared to the fully functional 412 bp promoter contained in RTJ133. These results indicate that promoter element 6 is necessary for promoter activity. In summary, these results indicate that the Genomatix analysis set forth in Example 6 identified multiple elements necessary for this promoter to drive nematode-induced transcription in the feeding site.

What is claimed is:

1. A promoter comprising an isolated nucleic acid capable of driving root-specific and/or nematode-inducible expression of a second nucleic acid selected from the group consisting of a nucleic acid having a sequence as set forth in SEQ ID NO:1;

a nucleic acid comprising nucleotides 1554 to 1887 of a sequence as set forth in SEQ ID NO:1;

a nucleic acid comprising nucleotides 1318 to 1967 of a sequence as set forth in SEQ ID NO:1;

a nucleic acid comprising nucleotides 1526 to 1967 of a sequence as set forth in SEQ ID NO:1;

a nucleic acid comprising nucleotides 1556 to 1967 of a sequence as set forth in SEQ ID NO:1;

a nucleic acid having a sequence as set forth in SEQ ID NO:3; and a nucleic acid comprising nucleotides 364 to 697 of a sequence as set forth in SEQ ID NO:3.

2. An expression cassette comprising the nucleic acid of claim 1.

3. A transgenic plant comprising the expression cassette of claim 2.

4. The transgenic plant of claim 3, wherein the plant is a monocot.

5. The transgenic plant of claim 3, wherein the plant is a dicot.

6. The transgenic plant of claim 3, wherein the plant is selected from the group consisting of soybean, potato, tomato, peanuts, cotton, cassaya, coffee, coconut, pineapple, citrus trees, banana, corn, rape, beet, sunflower, sorghum, wheat, oats, rye, barley, rice, green bean, lima bean, pea, and tobacco.

7. The transgenic plant of claim 3, wherein the plant is a whole plant, a plant cell, a plant part, or a plant seed.

8. A plant seed produced by the transgenic plant of claim 3, wherein the seed comprises the isolated nucleic acid.

9. The expression cassette of claim 2, which further comprises a nucleic acid encoding an agent that disrupts metabolism, growth, and/or reproduction of a plant parasitic nematode that confers or improves plant resistance to a plant parasitic nematode or that is toxic to a plant parasitic nematode.

10. A vector comprising the isolated nucleic acid of claim 1.

11. A plant cell comprising the isolated nucleic acid of claim 1, or an expression cassette or vector comprising the nucleic acid.

12. A method of controlling a parasitic nematode infestation in plants, comprising the step of growing a plant from seed comprising an expression cassette comprising the isolated nucleic acid of claim 1 in operative association with a second nucleic acid that encodes an agent that disrupts metabolism, growth, and/or reproduction of said plant parasitic nematode, that confers or improves plant resistance to said plant parasitic nematode, or that is toxic to said plant parasitic nematode, wherein the expression cassette is stably integrated into the genome of the seed.

13. A method of conferring or improving nematode resistance in a plant, comprising a) preparing a construct comprising a first nucleic acid comprising the nucleic acid sequence of claim 1 operably linked to a second nucleic acid,
b) transforming a plant cell with the construct of a) wherein the first nucleotide sequence induces transcription of the second nucleotide sequence in a plant cell in response to a nematode stimulus; and
c) regenerating the transformed plant cell to produce a transgenic plant having nematode resistance or improved resistance.

14. The method of claim 13, wherein the second nucleic acid encodes an agent that disrupts metabolism, growth, and/or reproduction of a plant parasitic nematode that confers or improves plant resistance to a plant parasitic nematode, or that is toxic to a plant parasitic nematode.

15. A method for production of a transgenic plant being resistant or having improved resistance to plant parasitic nematodes comprising transforming a plant cell with the promoter of claim 1 or an expression cassette or vector comprising the promoter and regenerating the transformed plant cell to produce a transgenic plant being resistant or having improved resistance.

16. An expression cassette comprising a nucleic acid inducible by plant nematodes, selected from the group consisting of a nucleic acid having a sequence as set forth in SEQ ID NO:2; and
a nucleic acid comprising nucleotides 1569 to 1902 of a sequence as set forth in SEQ ID NO:2;
which further comprises a nucleic acid encoding an agent that disrupts metabolism, growth, and/or reproduction of a plant parasitic nematode that confers or improves plant resistance to a plant parasitic nematode or that is toxic to a plant parasitic nematode.

17. A transgenic plant comprising the expression cassette of claim 16.

* * * * *

UNITED STATES PATENT AND TRADEMARK OFFICE
CERTIFICATE OF CORRECTION

| | | |
|---|---|---|
| PATENT NO. | : 8,053,630 B2 | Page 1 of 1 |
| APPLICATION NO. | : 12/280186 | |
| DATED | : November 8, 2011 | |
| INVENTOR(S) | : Aaron Wiig et al. | |

It is certified that error appears in the above-identified patent and that said Letters Patent is hereby corrected as shown below:

On the Title Page, item (12) should read; Wiig et al.

On the Title Page, In Item (75), line 1, "Inventors: Aaron Wig, Chapel Hill, NC (US);" should read -- Inventors: Aaron Wiig, Chapel Hill, NC (US); --

In claim 6, at column 47, line number 5, "tomato, peanuts, cotton, cassaya, coffee, coconut, pineapple," should read -- tomato, peanuts, cotton, cassava, coffee, coconut, pineapple, --

Signed and Sealed this
Thirteenth Day of March, 2012

David J. Kappos
*Director of the United States Patent and Trademark Office*

SEQUENCE LISTING

<160> NUMBER OF SEQ ID NOS: 34

<210> SEQ ID NO 1
<211> LENGTH: 1967

<212> TYPE: DNA
<213> ORGANISM: Arabidopsis thaliana
<220> FEATURE:
<221> NAME/KEY: promoter
<222> LOCATION: (1)..(1887)

<400> SEQUENCE: 1

```
cagacaaaga attattggaa aacaatgaga attttttgacg gtggtttgtt ataatgtatt    60
attaaataac atgataatgg aaattacttt gttttagtta aaggaaaatt aatttgttgt   120
ttaataaact agtggtaggt aggaatagtt aaaatgtaag tatcaaagtt tttttgaattt  180
aagattaaga ttctcgaaat tcagttatta gcatacaaat gacataaatt atgaaaaaat   240
aaattaaaat aatgtcatac agatccagat gaaaatgtat aatgtatata catttgataa   300
aaatgaaaat gtattttcgg gttctcagtt tgttttgtga aatatcaata cacaatgtta   360
aaaagaatc ggcttcttc agcttatgat attcattaat tttccacaca ccatttttca    420
aagggaaata gcaaaaaaaa ttaaaattaa aacagccagc taaattaatc agtgaaatca   480
tccaaactgt tttacaaaga catttttttcg gccaaatcaa ataaaaaaat cgattgttat   540
tgacagtctt tgtgatctta ttggttacgt tatacccacc tgtgcactcc acttttaagt   600
actacttcgt ctctaaatat ggtacggact aacttgaaat tagcctattg atttgcttag   660
aaattgataa atctttggac gagatggtgt ccactcttta aatcaccaca atgtccccta   720
tctatttttcc gcgacaagat gaataagaat atgcactaaa cttaaccatc attcgcttat   780
acactatatt tattaaatca gctttctcat cgcctaaaat tcaatatttt tgggtccatt   840
atctacacga cacaatggat cattcacata cggccgcgca tcaaatgatt tcgtaagtcc   900
cggcaaatgt taataaacta tttgaaaaag aaagagtcat gtgtcccgtc aattcaagta   960
cttatttatt gtgatttttt gcacatatat agattaacat atattcatgg ttaaaacttg  1020
ttgatgctgc aaaaaggata attatcaccc acgtacatta ctcatatgaa tataaaaggt  1080
gcataatttt tttttttttt tttgtaatgt tttatgtata tacacatata gtataccaat  1140
tttttaacaa aacaaattac atatagataa caaagaggtg aatagtttcg atcgtgaata  1200
ttcaggttga tactaattag ttctcctttt gtagattcga caagtgtgat gagtggataa  1260
aaaaatggat gacgtcttga gtggattgta catatacaaa tagataatgt aagtgcatgc  1320
tttttgattc ttcgaaacta tttggttata actttcggat atacttataa caaaaaaaaa  1380
aacctttcgg atatacatgg ttcggcttgg acgtacaggt ctatataata atttgatata  1440
tattggtaca tttcatttat atactcttta ttggtacgat acattttgat tcgttatcaa  1500
tatattaata ccacattgac gagaacattc tcattagtga tcgtagatta ataatctagc  1560
catcttaata agcaaaatat ataatccaaa aaatgcgaca ttattttaca tacgcaagtg  1620
ttcacaacca atagtccaat atataaatta attaagtagg tatgtaatat aaccaaggaa  1680
attacgatct aatccagttt tgattaccta gaacaagacc atagttagcc acacataatg  1740
gatacgtgct tgacaacaat taaaaaccta tatttttaaa agtgatgctt aaatagccaa  1800
tggattgaaa tgtgcactcg catatattgc tttttgtgtc agcacaattt ggctatataa  1860
gcaagtactc tcttgtagta atcattcaca gtcataacta attaagtaca tttgaataca  1920
tcaaatacca agaagagaa atttagagag aaagagaaag agataaa                 1967
```

<210> SEQ ID NO 2
<211> LENGTH: 1947
<212> TYPE: DNA
<213> ORGANISM: Arabidopsis thaliana
<220> FEATURE:

```
<221> NAME/KEY: promoter
<222> LOCATION: (1)..(1902)

<400> SEQUENCE: 2
cactaatata agacatggca cgtttgcatt atgcttccta tattaccgac taaattagtg      60
attgtcacaa gtagccgaca acttttggac ttaattagca acagacttat tgcttcagta     120
agaaaccaac agataagcga tgggcataaa tggtatgtgg cttttcatc ctgttttcat      180 gttttgaacg tcaagaaaaa aaattaataa gggattttttg aatccatccc gtacgtttta    240
tatttataaa tagtttagat aaaccttaat tcctcaacta aatactagtt tcttggcatc    300
ttataaagaa actatatgca tttttatccc taataatata gtctgtagcg tatttgcctc    360
catatattat cgccatatta tcatagactg catctcattt agggcgaatg taatcatagt    420
ttttgtaaag aattgaacta cctcttcgcc tttttttta tataagacaa ttctttagtt      480
tctatctatg gtttaatttg tattttgacg tgtatggtac taattaagat tatgctatgt    540
tttgagtttt agttgaataa aatttaattt gtaataattc taaaacaata aaagtttag    600 tgtaatttt tttaactaga acggattaag agttaggact gatgttagaa tcgcagtttt    660 tttttatgg aatgacgtaa aagaattctt taataatctt acttggcaat attaaatgga    720
acaacttaaa aggactagac aatattattg gcgtgatatc caaataatta cggtttaaca    780
aagaataaaa tggggaaacc ctttggtata ttggttatct aagagttcat taatatttat    840
atacattaag aggttagagt ttcgaggtca agatattatg tttatttaaa aatttgcaga    900
ttaatagaga caagtgtgta ggagatctcc aacgatattc aattataacc gttcgtcaga    960
attctacgca gatagaacgt cgttaggtca tagatcattg aaagtgtcta tcaaaagcat   1020
ggagattaaa aaagaaaaaa gatttggaga aagaagtgac ttttgtcctg gatctattaa   1080
gagtcgaaag aaatcgtccg ttatacaatc gtgtatataa caattctcat aatttacaat   1140
ttataatacc gaaaaatat aaaacaaaaa aaaatatttt taaatagaac gaatcagcct   1200
caacaaaaac cttttttgaa aatggaaaag cttaggctgc tttaacacgc ccaatctcac   1260
acatacatat tctctgtttt cttctttcct ttttgtaaaa gggtttgcta attctctgct   1320
ttgttttttt tttgtttatt aattctttac atttcctaca aagaaaaaga caagcatgaa   1380
taactaacag cggttatact ggaaatccga agtcttttcc acgtgctttc tgatgaacat   1440
ttaacataaa acgttcggac tcttcgtgac acttaaacca aacatacacg tacgtagcta   1500
acaatagacg tgtagatttt aggtttacgt gttttttcaag ttgggcaaga acaaaaaaaa   1560
agagagccta tgacgtgtgc aacaggataa tagtgttagc aaaagaaatc atcagagcca   1620
ttatatgata ttgtttgctt ttcaattcca tgaacgaacc cataccaatc caaaacagca   1680
attatcatct ttctttattg aacaaacgta tctcattggt cgtgtcctaa taaataatta   1740
tatttcatat acatgtatat actttatagt ttttgttttt ccttttgcta ctctacatga   1800
ctctcgatcg agggaaaaaa ctagttctca tgtttatcca aaactctata tcacctttt    1860 gatgttttta tataagaaga cttgttcatc catactcttt caataacctt gacagaaaaa   1920
aaaaataaac acaaaatttc aataacc                                       1947

<210> SEQ ID NO 3
<211> LENGTH: 791
<212> TYPE: DNA
<213> ORGANISM: Glycine max
<220> FEATURE:
<221> NAME/KEY: promoter
<222> LOCATION: (1)..(697)
```

```
<400> SEQUENCE: 3
ggttacagta ccaattctga aaaaacttaa tgtttagata aacttttta aaaaaaatac    60 tattcgactt gtttaaagtt aatgatatga aataaaattt tctatgaatt acttttgag   120 taaaaccata tatgtgtaca gcaaagtttg agaataatta atctcgatgg gaagaagaaa   180
aaaatgaaag tatgaaataa gatggatgat tggataaact aaaagagatg aaaaaatata   240
tatataaatt attacaaaaa aaaaaaatca tacaagaatg acattactga agcaaattcg   300
ctttcacatg aaaagtatgc agtgtaaaga tataaaagta aaccattatt tttgtcacta   360
aaaaatggat acagaaaacc gaacattaaa acatgatcat tcattcacca ttttaaaatt   420
aagatgatta atttaaataa aaaaatcata ttagataagt gatcaaaata ttagatagta   480
taaattaatt cacgtaacat acacgcatta atcgcgcttc ttgaatgatt agtcagcaat   540
taaaccgtgc taatttcttt tctcaccttc taatcttacc gctgccggga acgtgtaaat   600
taagtagcat tgtaaagcag cttttttggat tataaatatt attaaatata ctcacgggtt   660
gggtataaat attaagatgg ccagcattgg tttcgcaggg agttgcagat aaacaaaatc   720
tagcaggagc aaattcactt ctaagataca catattaagt tcaccagaga gagagagaga   780
cattaatcaa g                                                      791

<210> SEQ ID NO 4
<211> LENGTH: 1435
<212> TYPE: DNA
<213> ORGANISM: Glycine max

<400> SEQUENCE: 4
cacacaagca aattcacttc tctgttctga cacacatatt aagttcccga gaaagatcta    60
gagagtaatt aagatgggta cgtggttcac aaatgcaagg ccgtatctgc tgttagtggc   120
agttcaattt gggtctgctg gcatgttcat atttgcgatg gatgctataa agaagggtat   180
gagccattac gtgttcatcg tctatcgtaa tgccatcgcc tctgtatctc ttgctcccct   240
cgcatttgtt cttgaaagga agttaggcc caagatgact ttccgggtat tttcagagat   300
tatggcactg gctttcttcg aaataatact ggaccagtgc ttcgccctct ggggcatgaa   360
attcacgtcg gcatctttcc tatctgctgt tatgaactcc gctccctctg ttacttttgt   420
gatggctgtc attctaagaa tggagcacat gaagattaag gaggtggcat gtcaagccaa   480
agtgattggc acagtaataa catttggagg caccttgctt atggcactgt acaaaggacc   540
cgttcttagt tttatgcgat cttcaactag ccatcctagc caacctgaga atgtggccac   600
agaaactggt aaccattggg tcatagggac attgttcctc ctcattggtt gtgctggctt   660
ttctgcattt tacatattac aggccataac attggagaaa tacccagcag agatgtctct   720
ggccacttgg gtttgctttg taggagcact tcaaagctct attgttgcaa tcttcgcaga   780
acgccaccac cctcatgctt ggtcccttgg ttgggataca cgtctctttg ctcctgctta   840
cgcgggaata gttacgtctg gagttcagta ttacatacaa ggcatggtct caaaaattat   900
gggcccagtt attgtgactg ctttaatcc cctgcgtatg atcattgtta cggccttggc   960
ctgcatcatc ttatctgaac aactcttcct tggaagtatt attggagcaa tagttgtggt  1020
tcttgggctt tatctagttg tgtggggaaa agctaaagaa cgtagaggtc tgatgacacc  1080
gtcccctgca gaaaataact ttccagaaga ccaacgacag ctaccggtca cagctccaag  1140
gaatgatagc attaacaata taataaggc ttaattagtc catcgccatg atgaaaaaag  1200
tgatgtggaa ggcacaatat atcaagaaga gaaagtcagc aaaattttaag taaaggcctc  1260
```

| | |
|---|---:|
| ggctttgttt aattagacat tgttgtagca ttccatacaa atgatctaag gtcaatgtca | 1320 |
| tgcacattac taataccatg aaattggtgg gataagtggc atgacgattg atgaaattca | 1380 |
| tcatatatat aattaattag tggtcacttt gagctgcaaa aaaaaaaaaa aaaaa | 1435 |

<210> SEQ ID NO 5
<211> LENGTH: 871
<212> TYPE: DNA
<213> ORGANISM: Glycine max

<400> SEQUENCE: 5

| | |
|---|---:|
| ttcaaagctc tattgttgca atcttcgcag aacgccacca ccctcatgct tggtcccttg | 60 |
| gttgggatac acgactcttt gctcctgctt acgcgggaat agttacatct ggagttcagt | 120 |
| attacataca aggcatggtc tcaaaaatta tgggcccagt tattgtgact gcttttaatc | 180 |
| ccctgcgtat gatcattgtt acggccttgg cctgcatcat cttatccgag caactcttcc | 240 |
| ttggaagtat tattggagca gtagttgtgg ttcttgggct ttatctagtt gtgtggggaa | 300 |
| aagctaaaga acgcagaggt attatgacac cgtcccctgc agaaaataac tttccggaag | 360 |
| accaacgaca gctaccagtc atagctccaa ggaatgataa cattaatact aataaggctt | 420 |
| aattagtcct tcgccatgtt gaaaaaactg atgtggaagg cacaatatat caagaagaga | 480 |
| gagtcagtaa aatttaagta taggcctagg ctttgtttaa ttagacattg gtgtagcatt | 540 |
| ccgtacaagt gatctcaggt caatgtcatg cacattacta ataccatgaa atgggtggga | 600 |
| taagtggcat gacgattggt gaaattcatc atatatataa ttaattagtg atcaattaga | 660 |
| gctgcatcat tgttcttgag ttgaatgaac taatgtgctt ccgagtcatc atagagtaat | 720 |
| tatttacaca gttctgggct aatttgcttt catattccac ttttaagtat tccaattcag | 780 |
| ggctataaaa aaaatgtatt ccatttaagc taaggttgga gattttaata caagtctaaa | 840 |
| catatatttt tagcaaaaaa aaaaaaaaaa a | 871 |

<210> SEQ ID NO 6
<211> LENGTH: 1263
<212> TYPE: DNA
<213> ORGANISM: Glycine max

<400> SEQUENCE: 6

| | |
|---|---:|
| actatagggc acgcgtggtc gacggcccgg gctggtatca taattttatt tatttattta | 60 |
| tttattttg tgtctccatt ctattgtaaa aatgaaataa tgtaaaacga gttttgttat | 120 |
| tttatggtta cagtaccaat tctgaaaaaa cttaatgttt agataaactt ttttaaaaaa | 180 |
| aatactattc gacttgttta aagttaatga tatgaaataa aatttctat gaattacttt | 240 |
| ttgagtaaaa ccatatatgt gtacagcaaa gtttgagaat aatttatctc gatgggaaga | 300 |
| agaaaaaaat gaaagtatga aataagatgg atgattggat aaactaaaag agatgaaaaa | 360 |
| atatatatat aaattattac aaaaaaaaaa atcatacaa gaatgacatt actgaagcaa | 420 |
| attcgctttc acatgaaaag tatgcagtgt aaagatataa aagtaaacca ttattttgt | 480 |
| cactaaaaaa tggatacaga aaaccgaaca ttaaaacatg atcattcatt caccatttta | 540 |
| aaattaagat gattaattta aataaaaaaa tcatattaga taagtgatca aaatattaga | 600 |
| tagtataaat taattcacgt aacatacacg cattaatcgc gcttcttgaa tgattagtca | 660 |
| gcaattaaac cgtgctaatt tctttttctca ccttctaatc ttaccgctgc cgggaacgtg | 720 |
| taaattaagt agcattgtaa agcagctttt tggattataa atattattaa atatactcac | 780 |
| gggttgggta taaatattaa gatggccagc attggtttcg cagggagttg cagataaaca | 840 |

```
aaatctagca ggagcaaatt cacttctaag atacacatat taagttcacc agagagagag    900
agagacatta atcaagatgg gtacgtggtt cacaaatgca aggccgtatc tgctgttagt    960
ggcggttcaa tttggctcag caggcatgtt catatttgcg atggatgcta taagaagggg   1020
tatgagccat tacgtgttca tcgtctatcg taatgccatc gcctctgtat ctcttgctcc   1080
cttcgcattc gttttagaaa ggtctcttcc ccttacttct catccatgca tgcatataca   1140
tcaaagtgta tatatatgta tatatatata tattcacctc tattaaatta aattaaaaga   1200
aatactattg tttaattttg caggaaaatt aggcccaaga tgactttccg ggtattttca   1260
gag                                                                 1263
```

<210> SEQ ID NO 7
<211> LENGTH: 35
<212> TYPE: DNA
<213> ORGANISM: Artificial Sequence
<220> FEATURE:
<223> OTHER INFORMATION: Description of Artificial sequence: oligo
      primer

<400> SEQUENCE: 7

```
ctgcagcaga caaagaatta ttggaaaaca atgag                              35
```

<210> SEQ ID NO 8
<211> LENGTH: 40
<212> TYPE: DNA
<213> ORGANISM: Artificial Sequence
<220> FEATURE:
<223> OTHER INFORMATION: Description of Artificial sequence: oligo
      primer

<400> SEQUENCE: 8

```
ggcgcgcctt tatctctttc tctttctctc taaatttctc                         40
```

<210> SEQ ID NO 9
<211> LENGTH: 32
<212> TYPE: DNA
<213> ORGANISM: Artificial Sequence
<220> FEATURE:
<223> OTHER INFORMATION: Description of Artificial sequence: oligo
      primer

<400> SEQUENCE: 9

```
ctgcagcact aatataagac atggcacgtt tg                                 32
```

<210> SEQ ID NO 10
<211> LENGTH: 43
<212> TYPE: DNA
<213> ORGANISM: Artificial Sequence
<220> FEATURE:
<223> OTHER INFORMATION: Description of Artificial sequence: oligo
      primer

<400> SEQUENCE: 10

```
ggcgcgccgg ttattgaaat tttgtgttta tttttttttt ctg                     43
```

<210> SEQ ID NO 11
<211> LENGTH: 31
<212> TYPE: DNA
<213> ORGANISM: Artificial Sequence
<220> FEATURE:
<223> OTHER INFORMATION: Description of Artificial sequence: oligo
      primer

<400> SEQUENCE: 11

```
gataggaaag atgccgacgt gaatttcatg c                                  31
```

<210> SEQ ID NO 12
<211> LENGTH: 29
<212> TYPE: DNA
<213> ORGANISM: Artificial Sequence
<220> FEATURE:
<223> OTHER INFORMATION: Description of Artificial sequence: oligo
      primer

<400> SEQUENCE: 12
ctctgaaaat acccggaaag tcatcttgg                              29

<210> SEQ ID NO 13
<211> LENGTH: 22
<212> TYPE: DNA
<213> ORGANISM: Artificial Sequence
<220> FEATURE:
<223> OTHER INFORMATION: Description of Artificial sequence: oligo
      primer

<400> SEQUENCE: 13
gtaatacgac tcactatagg gc                                     22

<210> SEQ ID NO 14
<211> LENGTH: 19
<212> TYPE: DNA
<213> ORGANISM: Artificial Sequence
<220> FEATURE:
<223> OTHER INFORMATION: Description of Artificial sequence: oligo
      primer

<400> SEQUENCE: 14
actatagggc acgcgtggt                                         19

<210> SEQ ID NO 15
<211> LENGTH: 25
<212> TYPE: DNA
<213> ORGANISM: Artificial Sequence
<220> FEATURE:
<223> OTHER INFORMATION: Description of Artificial sequence: oligo
      primer

<400> SEQUENCE: 15
ctgcagggtt acagtaccaa ttctg                                  25

<210> SEQ ID NO 16
<211> LENGTH: 29
<212> TYPE: DNA
<213> ORGANISM: Artificial Sequence
<220> FEATURE:
<223> OTHER INFORMATION: Description of Artificial sequence: oligo
      primer

<400> SEQUENCE: 16
ggcgcgccct tgattaatgt ctctctctc                              29

<210> SEQ ID NO 17
<211> LENGTH: 15
<212> TYPE: DNA
<213> ORGANISM: Artificial Sequence
<220> FEATURE:
<223> OTHER INFORMATION: Description of Artificial sequence: consensus
      sequence
<220> FEATURE:
<221> NAME/KEY: misc_feature
<223> OTHER INFORMATION: w is a, or t
<220> FEATURE:
<221> NAME/KEY: misc_feature
<223> OTHER INFORMATION: r is a, or g

```
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 17
tnccawawwt rgnaa                                                        15

<210> SEQ ID NO 18
<211> LENGTH: 14
<212> TYPE: DNA
<213> ORGANISM: Artificial Sequence
<220> FEATURE:
<223> OTHER INFORMATION: Description of Artificial sequence: consensus
      sequence
<220> FEATURE:
<221> NAME/KEY: misc_feature
<223> OTHER INFORMATION: w is a, or t
<220> FEATURE:
<221> NAME/KEY: misc_feature
<223> OTHER INFORMATION: k is g, or t
<220> FEATURE:
<221> NAME/KEY: misc_feature
<223> OTHER INFORMATION: s is c, or g
<220> FEATURE:
<221> NAME/KEY: misc_feature
<223> OTHER INFORMATION: y is c, or t
<220> FEATURE:
<221> NAME/KEY: misc_feature
<223> OTHER INFORMATION: m is a, or c
<220> FEATURE:
<221> NAME/KEY: misc_feature
<222> LOCATION: (12)..(12)
<223> OTHER INFORMATION: n is a, c, g, or t

<400> SEQUENCE: 18
swsktatcca tnym                                                         14

<210> SEQ ID NO 19
<211> LENGTH: 9
<212> TYPE: DNA
<213> ORGANISM: Artificial Sequence
<220> FEATURE:
<223> OTHER INFORMATION: Description of Artificial sequence: consensus
      sequence
<220> FEATURE:
<221> NAME/KEY: misc_feature
<223> OTHER INFORMATION: w is a, or t
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 19 wnwaaagng                                                                9

<210> SEQ ID NO 20
<211> LENGTH: 6
<212> TYPE: DNA
<213> ORGANISM: Artificial Sequence
<220> FEATURE:
<223> OTHER INFORMATION: Description of Artificial sequence: consensus
      sequence

<400> SEQUENCE: 20
```

```
ccacgt                                                             6

<210> SEQ ID NO 21
<211> LENGTH: 6
<212> TYPE: DNA
<213> ORGANISM: Artificial Sequence
<220> FEATURE:
<223> OTHER INFORMATION: Description of Artificial sequence: consensus
      sequence

<400> SEQUENCE: 21 ttaatg                                                             6

<210> SEQ ID NO 22
<211> LENGTH: 15
<212> TYPE: DNA
<213> ORGANISM: Artificial Sequence
<220> FEATURE:
<223> OTHER INFORMATION: Description of Artificial sequence: consensus
      sequence
<220> FEATURE:
<221> NAME/KEY: misc_feature
<223> OTHER INFORMATION: w is a, or t
<220> FEATURE:
<221> NAME/KEY: misc_feature
<223> OTHER INFORMATION: y is c, or t
<220> FEATURE:
<221> NAME/KEY: misc_feature
<223> OTHER INFORMATION: s is c, or g
<220> FEATURE:
<221> NAME/KEY: misc_feature
<223> OTHER INFORMATION: m is a, or c
<220> FEATURE:
<221> NAME/KEY: misc_feature
<222> LOCATION: (2)..(2)
<223> OTHER INFORMATION: n is a, c, g, or t

<400> SEQUENCE: 22
wncyaaaaat gsmaa                                                   15

<210> SEQ ID NO 23
<211> LENGTH: 8
<212> TYPE: DNA
<213> ORGANISM: Artificial Sequence
<220> FEATURE:
<223> OTHER INFORMATION: Description of Artificial sequence: consensus
      sequence

<400> SEQUENCE: 23 caattatt                                                           8

<210> SEQ ID NO 24
<211> LENGTH: 13
<212> TYPE: DNA
<213> ORGANISM: Artificial Sequence
<220> FEATURE:
<223> OTHER INFORMATION: Description of Artificial sequence: consensus
      sequence
<220> FEATURE:
<221> NAME/KEY: misc_feature
<223> OTHER INFORMATION: y is c, or t
<220> FEATURE:
<221> NAME/KEY: misc_feature
<223> OTHER INFORMATION: m is a, or c
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
```

```
<400> SEQUENCE: 24
ynmtataaat ana                                                    13

<210> SEQ ID NO 25
<211> LENGTH: 11
<212> TYPE: DNA
<213> ORGANISM: Artificial Sequence
<220> FEATURE:
<223> OTHER INFORMATION: Description of Artificial sequence: consensus
      sequence
<220> FEATURE:
<221> NAME/KEY: misc_feature
<223> OTHER INFORMATION: r is a, or g

<400> SEQUENCE: 25
gtaatgattr c                                                      11

<210> SEQ ID NO 26
<211> LENGTH: 6
<212> TYPE: DNA
<213> ORGANISM: Artificial Sequence
<220> FEATURE:
<223> OTHER INFORMATION: Description of Artificial sequence: consensus
      sequence
<220> FEATURE:
<221> NAME/KEY: misc_feature
<223> OTHER INFORMATION: w is a, or t

<400> SEQUENCE: 26 waaagc                                                             6

<210> SEQ ID NO 27
<211> LENGTH: 11
<212> TYPE: DNA
<213> ORGANISM: Artificial Sequence
<220> FEATURE:
<223> OTHER INFORMATION: Description of Artificial sequence: consensus
      sequence
<220> FEATURE:
<221> NAME/KEY: misc_feature
<223> OTHER INFORMATION: r is a, or g

<400> SEQUENCE: 27
gtaatgattr c                                                      11

<210> SEQ ID NO 28
<211> LENGTH: 31
<212> TYPE: DNA
<213> ORGANISM: Artificial Sequence
<220> FEATURE:
<223> OTHER INFORMATION: Description of Artificial sequence: oligo
      primer

<400> SEQUENCE: 28
ccaactgcag tgcttttga ttcttcgaaa c                                 31

<210> SEQ ID NO 29
<211> LENGTH: 31
<212> TYPE: DNA
<213> ORGANISM: Artificial Sequence
<220> FEATURE:
<223> OTHER INFORMATION: Description of Artificial sequence: oligo
      primer

<400> SEQUENCE: 29
atgcctgcag cattctcatt agtgatcgta g                                31

<210> SEQ ID NO 30
```

-continued

```
<211> LENGTH: 28
<212> TYPE: DNA
<213> ORGANISM: Artificial Sequence
<220> FEATURE:
<223> OTHER INFORMATION: Description of Artificial sequence:  oligo
      primer

<400> SEQUENCE: 30
atgcctgcag ctagccatct taataagc                                            28

<210> SEQ ID NO 31
<211> LENGTH: 31
<212> TYPE: DNA
<213> ORGANISM: Artificial Sequence
<220> FEATURE:
<223> OTHER INFORMATION: Description of Artificial sequence:  oligo
      primer

<400> SEQUENCE: 31
atgcctgcag attttacata cgcaagtgtt c                                        31

<210> SEQ ID NO 32
<211> LENGTH: 31
<212> TYPE: DNA
<213> ORGANISM: Artificial Sequence
<220> FEATURE:
<223> OTHER INFORMATION: Description of Artificial sequence:  oligo
      primer

<400> SEQUENCE: 32
atgcctgcag taagtaggta tgtaatataa c                                        31

<210> SEQ ID NO 33
<211> LENGTH: 29
<212> TYPE: DNA
<213> ORGANISM: Artificial Sequence
<220> FEATURE:
<223> OTHER INFORMATION: Description of Artificial sequence:  oligo
      primer

<400> SEQUENCE: 33
atgcctgcag agaacaagac catagttag                                           29

<210> SEQ ID NO 34
<211> LENGTH: 17
<212> TYPE: DNA
<213> ORGANISM: Artificial Sequence
<220> FEATURE:
<223> OTHER INFORMATION: Description of Artificial sequence:  oligo
      primer

<400> SEQUENCE: 34
ggacgtaaca tgtcgac                                                        17
```